United States Patent
Majima et al.

(10) Patent No.: US 11,208,441 B2
(45) Date of Patent: Dec. 28, 2021

(54) IMMUNOGLOBULIN-BINDING POLYPEPTIDE

(71) Applicant: ProteNova Co., Ltd., Higashikagawa (JP)

(72) Inventors: Eiji Majima, Higashikagawa (JP); Atsushi Shima, Higashikagawa (JP)

(73) Assignee: PROTENOVA CO., LTD., Higashikagawa (JP)

( * ) Notice: Subject to any disclaimer, the term of this patent is extended or adjusted under 35 U.S.C. 154(b) by 514 days.

(21) Appl. No.: 15/770,150

(22) PCT Filed: Oct. 19, 2016

(86) PCT No.: PCT/JP2016/080977
§ 371 (c)(1),
(2) Date: Apr. 20, 2018

(87) PCT Pub. No.: WO2017/069158
PCT Pub. Date: Apr. 27, 2017

(65) Prior Publication Data
US 2018/0305414 A1    Oct. 25, 2018

(30) Foreign Application Priority Data
Oct. 22, 2015   (JP) .............................. JP2015-207864

(51) Int. Cl.
*C07K 14/315*  (2006.01)
*C07K 1/22*    (2006.01)
(Continued)

(52) U.S. Cl.
CPC .............. *C07K 14/315* (2013.01); *C07K 1/22* (2013.01); *C07K 14/195* (2013.01); *C07K 17/00* (2013.01);
(Continued)

(58) Field of Classification Search
CPC ...... C07K 14/315; C07K 1/22; C07K 14/195; C07K 17/00; C07K 17/10
See application file for complete search history.

(56) References Cited

U.S. PATENT DOCUMENTS 6,162,903 A    12/2000  Trowern et al.
6,831,161 B1   12/2004  Uhlén et al.
(Continued)

FOREIGN PATENT DOCUMENTS

EP    1 992 692 A1    11/2008
JP    H07-507925 A     9/1995
(Continued)

OTHER PUBLICATIONS

Supplemental European Search Report issued for Counterpart European Patent Appln. No. 16857471.3, (dated Apr. 24, 2019).
(Continued)

*Primary Examiner* — Daniel E Kolker
*Assistant Examiner* — James L Rogers
(74) *Attorney, Agent, or Firm* — Knobbe, Martens, Olson & Bear, LLP

(57) ABSTRACT

An object of the present invention is to provide a polypeptide having a high binding capacity for an immunoglobulin kappa chain, and having excellent alkali stability, by modifying an amino acid sequence of an immunoglobulin-binding domain of Protein L derived from *Peptostreptococcus magnus*. A polypeptide having a high binding capacity for an immunoglobulin kappa chain, and having excellent alkali stability can be obtained by substituting specific lysine residues in an immunoglobulin-binding domain of Protein L derived from *Peptostreptococcus magnus* 3316 strain, with a basic amino acid or a hydroxyl group-containing amino acid.

30 Claims, 1 Drawing Sheet
Specification includes a Sequence Listing.

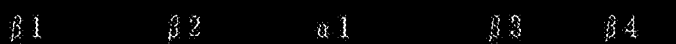

(51) Int. Cl.
  *C12N 15/11* (2006.01)
  *C12P 21/02* (2006.01)
  *C07K 17/00* (2006.01)
  *C07K 14/195* (2006.01)
  *C07K 17/10* (2006.01)

(52) U.S. Cl.
  CPC .............. *C07K 17/10* (2013.01); *C12N 15/11* (2013.01); *C12P 21/02* (2013.01); *C07K 2317/55* (2013.01); *C07K 2317/569* (2013.01); *C07K 2317/94* (2013.01); *C07K 2319/705* (2013.01)

(56) References Cited

U.S. PATENT DOCUMENTS

| | | |
|---|---|---|
| 2002/0137918 A1 | 9/2002 | Gore et al. |
| 2005/0100970 A1 | 5/2005 | Uhlen et al. |
| 2010/0130721 A1 | 5/2010 | Iwakura et al. |
| 2010/0286373 A1 | 11/2010 | Majima et al. |
| 2012/0177568 A1 | 7/2012 | Williams et al. |
| 2012/0301400 A1 | 11/2012 | Williams et al. |
| 2014/0113348 A1 | 4/2014 | Williams et al. |
| 2015/0030535 A1 | 1/2015 | Williams et al. |
| 2017/0320919 A1 | 11/2017 | Rodrigo et al. |
| 2017/0327535 A1* | 11/2017 | Yoshida ............... C07K 14/315 |
| 2017/0327545 A1 | 11/2017 | Rodrigo et al. |

FOREIGN PATENT DOCUMENTS

| | | |
|---|---|---|
| JP | 2006-304633 A | 11/2006 |
| JP | 2008-266219 A | 11/2008 |
| JP | 2015-501299 A | 1/2015 |
| JP | 2016-079149 A | 5/2016 |
| WO | WO 93/22438 A1 | 11/1993 |
| WO | WO 00/15803 A1 | 3/2000 |
| WO | WO 00/23580 A1 | 4/2000 |
| WO | WO 2007/097361 A1 | 8/2007 |
| WO | WO 2013/055404 A1 | 4/2013 |
| WO | WO 2016/096644 A1 | 6/2016 |

OTHER PUBLICATIONS

Bailey L.J. et al. "Applications for an engineered Protein-G variant with a pH controllable affinity to antibody fragments" Journal of Immunological Methods, vol. 415, Oct. 22, 2014, pp. 24-30.

General Electric Healthcare Bio-Sciences:"GE Healthcare Data file 29-0100-08 AB Affinity chromatography", Mar. 2012,pp. 1-8,Retrived from the Internet at: Wolfson.huji.ac.il/purification/PDF/affinity/GE_CaptoL.PDF.

Housden N.G. et al. "Immunoglobulin-biding domains: Protein L from *Peptostreptococcus magnus*", Biochemical Society Transactions, vol. 31, No. 3, Jun. 1, 2003 (Jun. 1, 2003), pp. 716-718.

Linhult M. et al. "Improving the tolerance of a protein A analogue to repeated alkaline exposures using a bypass mutagenesis approach", Proteins:Structure, Function, and Bioinformatics, vol. 55, No. 2, Feb. 27, 2004, pp. 407-416.

Sheng S. et al. "Separation of antigens and antibodies by immunoaffinity chromatography", Pharmaceutical Biology, vol. 50, No. 8, Apr. 6, 2012 (Apr. 6, 2012), pp. 1038-1044.

International Search Report for International Application No. PCT/JP2016/080977 dated Jan. 24, 2017 in 2 pages.

Protein Express Co., Ltd. 2015 downloaded from the world wide web at jst.go.jp/tt/fair/ij2015/exhibitor/group17/page1.html.

Kastern, et al. 1992 "Structure of Peptostreptococcal Protein L and Identification of a Repeated Immunoglobulin Light Chain-binding Domain" *The Journal of Biological Chemistry* 267(18): 12820-12825.

Minakuchi, et al. 2013 "Remarkable alkaline stability of an engineered protein A as immunoglobulin affinity ligand: C domain having only one amino acid substitution" *Protein Science* 22: 1230-1238.

Murphy, et al. 1994 "The functional units of a peptostreptococcal protein L" *Molecular Microbiology* 12(6): 911-920.

Graille, Marc, et al., "Complex between *Peptostreptococcus magnus* Protein L and a Human Antibody Reveals Structural Convergence in the Interaction Modes of Fab Binding Proteins," Structure, 2001, vol. 9, p. 679-687.

\* cited by examiner

Fig. 1

| Immunoglobulin-Binding Domain 1 : | ETP-EPEEBV TIKANLIFAD GSTQNAEFKG TFAKAVSDAY AYADALKKDN GEYTVDVADK GLTLNIKFAG |
| Immunoglobulin-Binding Domain 2 : | EKPEEPKEEV TIKVNLIFAD GKTQTAEFKG TFEEATAKAY AYADLLAKEN GEYTADLEDG GYTINIKFAG |
| Immunoglobulin-Binding Domain 3 : | ETPEEPKEEV TIKVNLIFAD GKIQTAEFKG TFEEATAKAY AYANLLAKEN GEYTADLEDG GYTINIKFAG |
| Immunoglobulin-Binding Domain 4 : | ETPEEPKEEV TIKVNLIFAD GKIQTAEFKG TFEEATAEAY RYADLLAKVN GEYTADLEDG GYTINIKFAG |
| Three-Dimensional Structure | β1 β2 α1 β3 β4 |

Fig. 2

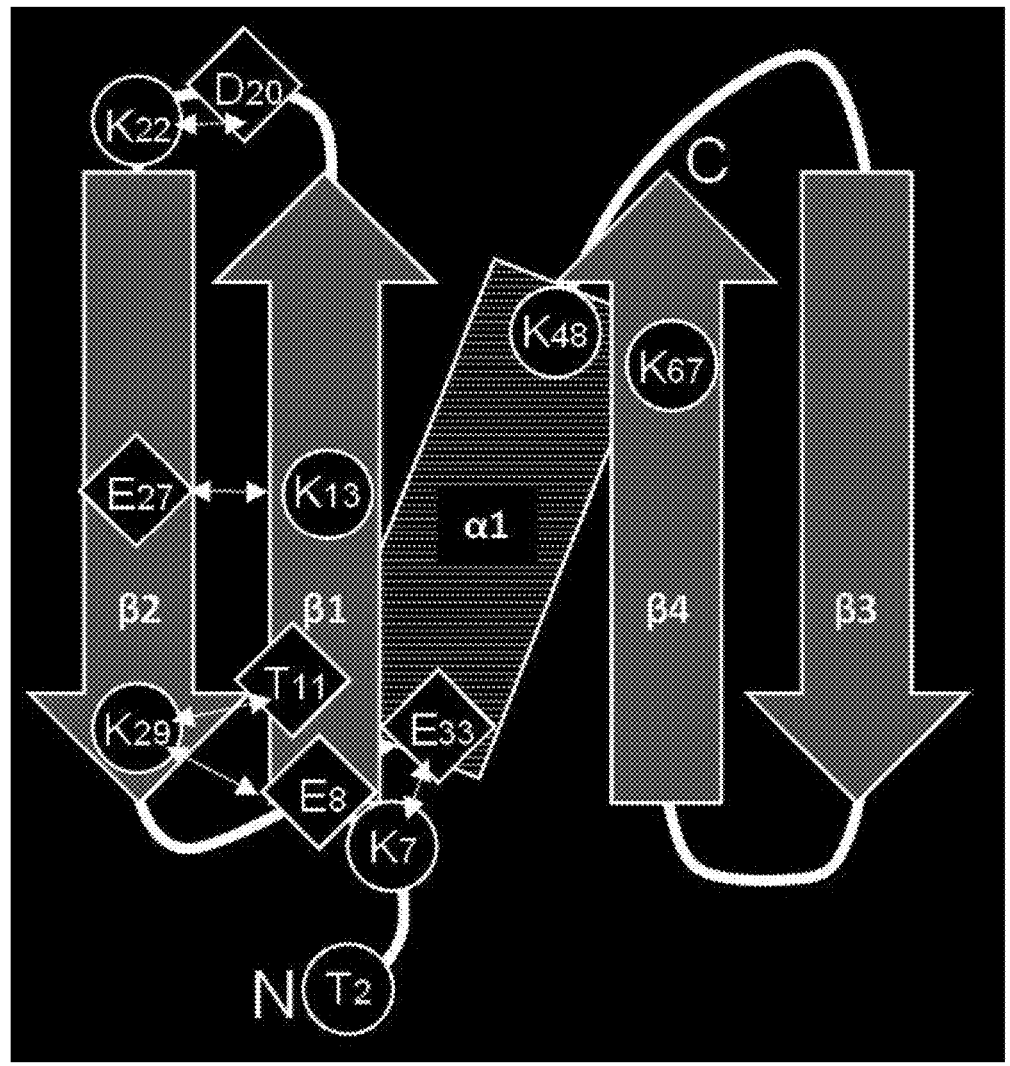

SEQUENCE LISTING

```
<160> NUMBER OF SEQ ID NOS: 39

<210> SEQ ID NO 1
<211> LENGTH: 70
<212> TYPE: PRT
<213> ORGANISM: Peptostreptococcus magnus

<400> SEQUENCE: 1

Glu Thr Pro Glu Glu Pro Lys Glu Glu Val Thr Ile Lys Val Asn Leu
1               5                   10                  15

Ile Phe Ala Asp Gly Lys Thr Gln Thr Ala Glu Phe Lys Gly Thr Phe
            20                  25                  30

Glu Glu Ala Thr Ala Glu Ala Tyr Arg Tyr Ala Asp Leu Leu Ala Lys
        35                  40                  45

Val Asn Gly Glu Tyr Thr Ala Asp Leu Glu Asp Gly Gly Tyr Thr Ile
    50                  55                  60

Asn Ile Lys Phe Ala Gly
65                  70

<210> SEQ ID NO 2
<211> LENGTH: 70
<212> TYPE: PRT
<213> ORGANISM: Peptostreptococcus magnus

<400> SEQUENCE: 2

Glu Thr Pro Glu Glu Pro Lys Glu Glu Val Thr Ile Lys Val Asn Leu
1               5                   10                  15

Ile Phe Ala Asp Gly Lys Ile Gln Thr Ala Glu Phe Lys Gly Thr Phe
            20                  25                  30

Glu Glu Ala Thr Ala Lys Ala Tyr Ala Tyr Ala Asn Leu Leu Ala Lys
        35                  40                  45

Glu Asn Gly Glu Tyr Thr Ala Asp Leu Glu Asp Gly Gly Asn Thr Ile
    50                  55                  60
```

Asn Ile Lys Phe Ala Gly
65                  70

<210> SEQ ID NO 3
<211> LENGTH: 70
<212> TYPE: PRT
<213> ORGANISM: Peptostreptococcus magnus

<400> SEQUENCE: 3

Glu Lys Pro Glu Glu Pro Lys Glu Glu Val Thr Ile Lys Val Asn Leu
1               5                   10                  15

Ile Phe Ala Asp Gly Lys Thr Gln Thr Ala Glu Phe Lys Gly Thr Phe
            20                  25                  30

Glu Glu Ala Thr Ala Lys Ala Tyr Ala Tyr Ala Asp Leu Leu Ala Lys
        35                  40                  45

Glu Asn Gly Glu Tyr Thr Ala Asp Leu Glu Asp Gly Gly Asn Thr Ile
    50                  55                  60

Asn Ile Lys Phe Ala Gly
65                  70

<210> SEQ ID NO 4
<211> LENGTH: 69
<212> TYPE: PRT
<213> ORGANISM: Peptostreptococcus magnus

<400> SEQUENCE: 4

Glu Thr Pro Glu Pro Glu Glu Val Thr Ile Lys Ala Asn Leu Ile
1               5                   10                  15

Phe Ala Asp Gly Ser Thr Gln Asn Ala Glu Phe Lys Gly Thr Phe Ala
            20                  25                  30

Lys Ala Val Ser Asp Ala Tyr Ala Tyr Ala Asp Ala Leu Lys Lys Asp
        35                  40                  45

Asn Gly Glu Tyr Thr Val Asp Val Ala Asp Lys Gly Leu Thr Leu Asn
    50                  55                  60

Ile Lys Phe Ala Gly
65

<210> SEQ ID NO 5
<211> LENGTH: 992
<212> TYPE: PRT
<213> ORGANISM: Peptostreptococcus magnus

<400> SEQUENCE: 5

Met Lys Ile Asn Lys Lys Leu Leu Met Ala Ala Leu Ala Gly Ala Ile
1               5                   10                  15

Val Val Gly Gly Gly Ala Asn Ala Tyr Ala Ala Glu Glu Asp Asn Thr
            20                  25                  30

Asp Asn Asn Leu Ser Met Asp Glu Ile Ser Asp Ala Tyr Phe Asp Tyr
        35                  40                  45

His Gly Asp Val Ser Asp Ser Val Asp Pro Val Glu Glu Ile Asp
    50                  55                  60

Glu Ala Leu Ala Lys Ala Leu Ala Glu Ala Lys Glu Thr Ala Lys Lys
65                  70                  75                  80

His Ile Asp Ser Leu Asn His Leu Ser Glu Thr Ala Lys Lys Leu Ala
                85                  90                  95

Lys Asn Asp Ile Asp Ser Ala Thr Thr Ile Asn Ala Ile Asn Asp Ile
            100                 105                 110

-continued

Val Ala Arg Ala Asp Val Met Glu Arg Lys Thr Ala Glu Lys Glu Glu
            115                 120                 125

Ala Glu Lys Leu Ala Ala Lys Glu Thr Ala Lys Lys His Ile Asp
    130                 135                 140

Glu Leu Lys His Leu Ala Asp Lys Thr Lys Glu Leu Ala Lys Arg Asp
145                 150                 155                 160

Ile Asp Ser Ala Thr Thr Ile Asn Ala Ile Asn Asp Ile Val Ala Arg
                165                 170                 175

Ala Asp Val Met Glu Arg Lys Thr Ala Glu Lys Glu Ala Glu Lys
            180                 185                 190

Leu Ala Ala Ala Lys Glu Thr Ala Lys Lys His Ile Asp Glu Leu Lys
            195                 200                 205

His Leu Ala Asp Lys Thr Lys Glu Leu Ala Lys Arg Asp Ile Asp Ser
    210                 215                 220

Ala Thr Thr Ile Asp Ala Ile Asn Asp Ile Val Ala Arg Ala Asp Val
225                 230                 235                 240

Met Glu Arg Lys Leu Ser Glu Lys Glu Thr Pro Glu Pro Glu Glu Glu
                245                 250                 255

Val Thr Ile Lys Ala Asn Leu Ile Phe Ala Asp Gly Ser Thr Gln Asn
                260                 265                 270

Ala Glu Phe Lys Gly Thr Phe Ala Lys Ala Val Ser Asp Ala Tyr Ala
    275                 280                 285

Tyr Ala Asp Ala Leu Lys Lys Asp Asn Gly Glu Tyr Thr Val Asp Val
            290                 295                 300

Ala Asp Lys Gly Leu Thr Leu Asn Ile Lys Phe Ala Gly Lys Lys Glu
305                 310                 315                 320

Lys Pro Glu Glu Pro Lys Glu Val Thr Ile Lys Val Asn Leu Ile
                325                 330                 335

Phe Ala Asp Gly Lys Thr Gln Thr Ala Glu Phe Lys Gly Thr Phe Glu
            340                 345                 350

Glu Ala Thr Ala Lys Ala Tyr Ala Tyr Ala Asp Leu Leu Ala Lys Glu
            355                 360                 365

Asn Gly Glu Tyr Thr Ala Asp Leu Glu Asp Gly Gly Asn Thr Ile Asn
    370                 375                 380

Ile Lys Phe Ala Gly Lys Glu Thr Pro Glu Thr Pro Glu Glu Pro Lys
385                 390                 395                 400

Glu Glu Val Thr Ile Lys Val Asn Leu Ile Phe Ala Asp Gly Lys Ile
                405                 410                 415

Gln Thr Ala Glu Phe Lys Gly Thr Phe Glu Glu Ala Thr Ala Lys Ala
            420                 425                 430

Tyr Ala Tyr Ala Asn Leu Leu Ala Lys Glu Asn Gly Glu Tyr Thr Ala
            435                 440                 445

Asp Leu Glu Asp Gly Gly Asn Thr Ile Asn Ile Lys Phe Ala Gly Lys
    450                 455                 460

Glu Thr Pro Glu Thr Pro Glu Glu Pro Lys Glu Glu Val Thr Ile Lys
465                 470                 475                 480

Val Asn Leu Ile Phe Ala Asp Gly Lys Thr Gln Thr Ala Glu Phe Lys
                485                 490                 495

Gly Thr Phe Glu Glu Ala Thr Ala Glu Ala Tyr Arg Tyr Ala Asp Leu
            500                 505                 510

Leu Ala Lys Val Asn Gly Glu Tyr Thr Ala Asp Leu Glu Asp Gly Gly
    515                 520                 525

Tyr Thr Ile Asn Ile Lys Phe Ala Gly Lys Glu Gln Pro Gly Glu Asn

```
                530             535             540
Pro Gly Ile Thr Ile Asp Glu Trp Leu Leu Lys Asn Ala Lys Glu Glu
545                 550                 555                 560

Ala Ile Lys Glu Leu Lys Glu Ala Gly Ile Thr Ser Asp Leu Tyr Phe
                565                 570                 575

Ser Leu Ile Asn Lys Ala Lys Thr Val Glu Gly Val Glu Ala Leu Lys
                580                 585                 590

Asn Glu Ile Leu Lys Ala His Ala Gly Glu Thr Pro Glu Leu Lys
                595                 600                 605

Asp Gly Tyr Ala Thr Tyr Glu Glu Ala Glu Ala Ala Lys Glu Ala
            610                 615                 620

Leu Lys Asn Asp Asp Val Asn Ala Tyr Glu Ile Val Gln Gly Ala
625                 630                 635                 640

Asp Gly Arg Tyr Tyr Val Leu Lys Ile Glu Val Ala Asp Glu Glu
                645                 650                 655

Glu Pro Gly Glu Asp Thr Pro Glu Val Gln Glu Gly Tyr Ala Thr Tyr
                660                 665                 670

Glu Glu Ala Glu Ala Ala Lys Glu Ala Leu Lys Glu Asp Lys Val
            675                 680                 685

Asn Asn Ala Tyr Glu Val Val Gln Gly Ala Asp Gly Arg Tyr Tyr Tyr
                690                 695                 700

Val Leu Lys Ile Glu Asp Lys Glu Asp Glu Gln Pro Gly Glu Glu Pro
705                 710                 715                 720

Gly Glu Asn Pro Gly Ile Thr Ile Asp Glu Trp Leu Leu Lys Asn Ala
                725                 730                 735

Lys Glu Asp Ala Ile Lys Glu Leu Lys Glu Ala Gly Ile Ser Ser Asp
                740                 745                 750

Ile Tyr Phe Asp Ala Ile Asn Lys Ala Lys Thr Val Glu Gly Val Glu
                755                 760                 765

Ala Leu Lys Asn Glu Ile Leu Lys Ala His Ala Glu Lys Pro Gly Glu
                770                 775                 780

Asn Pro Gly Ile Thr Ile Asp Glu Trp Leu Leu Lys Asn Ala Lys Glu
785                 790                 795                 800

Ala Ala Ile Lys Glu Leu Lys Glu Ala Gly Ile Thr Ala Glu Tyr Leu
                805                 810                 815

Phe Asn Leu Ile Asn Lys Ala Lys Thr Val Glu Gly Val Glu Ser Leu
                820                 825                 830

Lys Asn Glu Ile Leu Lys Ala His Ala Glu Lys Pro Gly Glu Asn Pro
                835                 840                 845

Gly Ile Thr Ile Asp Glu Trp Leu Leu Lys Asn Ala Lys Glu Asp Ala
            850                 855                 860

Ile Lys Glu Leu Lys Glu Ala Gly Ile Thr Ser Asp Ile Tyr Phe Asp
865                 870                 875                 880

Ala Ile Asn Lys Ala Lys Thr Ile Glu Gly Val Glu Ala Leu Lys Asn
                885                 890                 895

Glu Ile Leu Lys Ala His Lys Lys Asp Glu Glu Pro Gly Lys Lys Pro
                900                 905                 910

Gly Glu Asp Lys Lys Pro Glu Asp Lys Lys Pro Gly Glu Asp Lys Lys
                915                 920                 925

Pro Glu Asp Lys Lys Pro Gly Glu Asp Lys Lys Pro Glu Asp Lys Lys
                930                 935                 940

Pro Gly Lys Thr Asp Lys Asp Ser Pro Asn Lys Lys Lys Ala Lys
945                 950                 955                 960
```

Leu Pro Lys Ala Gly Ser Glu Ala Glu Ile Leu Thr Leu Ala Ala Ala
            965                 970                 975

Ala Leu Ser Thr Ala Ala Gly Ala Tyr Val Ser Leu Lys Lys Arg Lys
        980                 985                 990

<210> SEQ ID NO 6
<211> LENGTH: 3258
<212> TYPE: DNA
<213> ORGANISM: Peptostreptococcus magnus

<400> SEQUENCE: 6

| | | | | | | |
|---|---|---|---|---|---|---|
| tttggacagt | ggacgaaaca | agaacactga | tttaataaat | tggtgaaatt | cgattgttga | 60 |
| aatacctttt | tgggtagaaa | taactaagga | atggcaatat | aattgcttgg | aaacgaattt | 120 |
| gatttaaata | gcattaaatg | caaaaaattt | aaaaggagga | gacaaattcc | accctttata | 180 |
| aagggaagtt | tccattgtca | aaataatatg | aagattaata | agaaattatt | aatggctgca | 240 |
| cttgcaggag | caattgtagt | tggtggtgga | gctaacgctt | acgcagctga | agaagataac | 300 |
| actgataata | acctttcaat | ggatgaaatt | agtgatgctt | attttgatta | tcacggagat | 360 |
| gtttcagatt | cagtagatcc | tgtagaagaa | gaaatagacg | aagcattagc | aaaagcatta | 420 |
| gcagaagcta | agaaacagc | aaaaaaacat | atagattctt | taaatcattt | gtcagaaaca | 480 |
| gcaaaaaaat | tagctaagaa | tgatatagat | tcagctacta | ctattaatgc | aatcaatgac | 540 |
| atcgtagcaa | gagcagatgt | aatggaaaga | aaaacagctg | aaaagaaga | agcagaaaaa | 600 |
| ttagcagcag | caaagaaac | agcaagaaa | catatagatg | aattaaaaca | cttagcagac | 660 |
| aaaacaaaag | aattagctaa | gagagatata | gattcagcta | ctactattaa | tgcaatcaat | 720 |
| gacatcgtag | caagagcaga | tgtaatggaa | agaaaaacag | ctgaaaaaga | agaagcagaa | 780 |
| aaattagcag | cagcaaaaga | aacagcaaag | aaacatatag | atgaattaaa | acacttagca | 840 |
| gacaaaacaa | agaattagc | taagagagat | atagattcag | ctactactat | tgatgcaatc | 900 |
| aatgatatcg | tagctagagc | agatgtaatg | gaaagaaagt | tatctgaaaa | agaaacacca | 960 |
| gaaccagaag | aagaagttac | aatcaaagct | aacttaatct | ttgcagatgg | aagcacacaa | 1020 |
| aatgcagaat | tcaaaggaac | attcgcaaaa | gcagtatcag | atgcttacgc | ttacgcagat | 1080 |
| gctttaaaga | aagacaacgg | agaatatact | gtagacgttg | cagataaagg | cttaacttta | 1140 |
| aatattaaat | tcgctggtaa | aaaagaaaaa | ccagaagaac | aaaagaaga | agttacaatc | 1200 |
| aaagttaact | taatctttgc | agatggaaag | acacaaacag | cagaattcaa | aggaacattt | 1260 |
| gaagaagcaa | cagcaaaagc | ttatgcttat | gcagacttat | tagcaaaaga | aaatggcgaa | 1320 |
| tatacagcag | acttagaaga | tggtggaaac | acaatcaaca | ttaaatttgc | tggaaaagaa | 1380 |
| acaccagaaa | caccgaaga | accaaaagaa | gaagttacaa | tcaaagttaa | cttaatcttt | 1440 |
| gcagatggaa | agatacaaac | agcagaattc | aaaggaacat | ttgaagaagc | aacagcaaaa | 1500 |
| gcttatgctt | atgcaaactt | attagcaaaa | gaaaatggcg | aatatacagc | agacttagaa | 1560 |
| gatggtggaa | acacaatcaa | cattaaattt | gctggaaaag | aaacaccaga | aacaccagaa | 1620 |
| gaaccaaaag | aagaagttac | aatcaaagtt | aacttaatct | ttgcagatgg | aaaaacacaa | 1680 |
| acagcagaat | tcaaaggaac | atttgaagaa | gcaacagcga | agcttacag | atatgcagac | 1740 |
| ttattagcaa | aagtaaatgg | tgaatacaca | gcagacttag | aagatggcgg | atacactatc | 1800 |
| aacatcaaat | ttgctggaaa | agaacaacca | ggcgaaaatc | caggaatcac | aattgatgaa | 1860 |
| tggttattaa | agaatgctaa | agaagaagca | atcaaagaat | taaagaagc | aggaatcact | 1920 |

```
tctgatttat acttcagctt aatcaataaa gcaaaaacag ttgaaggcgt agaagcatta    1980
aagaacgaaa tcttaaaagc acacgctgga gaagaaacac cagaattaaa agatggatat    2040
gcaacatatg aagaagcaga agcagcagct aaagaagctt tgaaaaatga tgatgttaac    2100
aacgcatacg aaatagttca aggtgcagac ggaagatact actatgtatt aaagattgaa    2160
gttgcagacg aagaagaacc aggtgaagac actccagaag ttcaagaagg ttacgcaact    2220
tacgaagaag cagaagcagc agctaaagaa gcattaaaag aagataaagt taacaatgca    2280
tacgaagtag ttcaaggtgc agacggaaga tactactatg tattaaaaat cgaagataaa    2340
gaagatgaac aaccaggtga agaaccaggc gaaaacccag gaatcacaat tgatgaatgg    2400
ttattaaaga atgctaaaga agacgcaatc aaagaattaa agaagcagg aatcagttct    2460 gacatatact ttgatgcaat caacaaagca aaaacagtag aaggcgtaga agcgttaaag    2520
aacgaaatct taaagcaca cgctgaaaaa ccaggcgaaa acccaggaat cacaattgat    2580
gaatggttat aaagaatgc taagaagct gcaatcaaag aattaaaaga agcaggaatc    2640
actgctgaat atctattcaa cttaatcaac aaagcaaaaa cagtagaagg cgtagaatca    2700
ttaaagaacg aaatcttaaa agcacacgct gaaaaaccag gcgaaaaccc aggaatcaca    2760
attgatgaat ggttattaaa gaacgctaaa gaagatgcaa ttaaagaatt aaagaagca    2820 ggaattactt ctgacatata ctttgatgct atcaacaaag caaaaactat tgaaggcgta    2880
gaagcattaa agaatgaaat cttaaaggct cataaaaag atgaagaacc aggtaaaaaa    2940
ccaggtgaag acaaaaaacc agaagataaa aaaccaggtg aagataaaaa accagaagac    3000
aaaaaacctg gtgaagataa aaaaccagaa gacaaaaaac caggtaaaac agataaagat    3060
tctccaaata agaagaaaaa agctaaatta ccaaaagctg gtagcgaagc tgaaatctta    3120
acattagcag cagcagcttt atcaacagca gcaggtgctt acgtttcact taaaaaacgt    3180
aaataattaa tcttagataa agaatagatt aatataaaaa atgggactta taatagtccc    3240 atttttaat gcgaaaaa                                                  3258

<210> SEQ ID NO 7
<211> LENGTH: 210
<212> TYPE: DNA
<213> ORGANISM: Artificial Sequence
<220> FEATURE:
<223> OTHER INFORMATION: Modified DNA fragment of immunoglobulin kappa
      light chain binding domain 4 of protein L

<400> SEQUENCE: 7
gagaccccgg aagaaccgcg cgaggaagtg acgatccgcg ttaacctgat ctttgcggat     60
gggcgcaccc agacggctga attccgtggc accttcgaag aggcgaccgc ggaggcctac    120
cgctatgcag atcctctcgc caaggtgaac ggggaatata cggccgatct tgaggatggc    180
gggtatacga tcaacattaa atttgcgggg                                    210

<210> SEQ ID NO 8
<211> LENGTH: 60
<212> TYPE: DNA
<213> ORGANISM: Artificial Sequence
<220> FEATURE:
<223> OTHER INFORMATION: oligo-166

<400> SEQUENCE: 8
ctggcggggc tcgcattaga gaagccggaa gaaccgaagg aggaagtgac gatcaaggtt     60

<210> SEQ ID NO 9
```

```
<211> LENGTH: 58
<212> TYPE: DNA
<213> ORGANISM: Artificial Sequence
<220> FEATURE:
<223> OTHER INFORMATION: oligo-167

<400> SEQUENCE: 9
tgaattcagc cgtctgggtc ttcccatccg caaagatcag gttaaccttg atcgtcac       58

<210> SEQ ID NO 10
<211> LENGTH: 67
<212> TYPE: DNA
<213> ORGANISM: Artificial Sequence
<220> FEATURE:
<223> OTHER INFORMATION: oligo-168

<400> SEQUENCE: 10
tgaattcaaa ggcaccttcg aagaggcgac cgcggaggcc taccgctatg cagatctcct    60
cgccaag                                                              67

<210> SEQ ID NO 11
<211> LENGTH: 67
<212> TYPE: DNA
<213> ORGANISM: Artificial Sequence
<220> FEATURE:
<223> OTHER INFORMATION: oligo-169

<400> SEQUENCE: 11
tgttgatcgt atacccgcca tcctcaagat cggccgtata ttccccgttc accttggcga    60
ggagatc                                                              67

<210> SEQ ID NO 12
<211> LENGTH: 11
<212> TYPE: PRT
<213> ORGANISM: Artificial Sequence
<220> FEATURE:
<223> OTHER INFORMATION: Artifical sequence of N-terminal

<400> SEQUENCE: 12

Met Ala Gln His Asp Glu Ala Gly Leu Ala Leu
1               5                   10

<210> SEQ ID NO 13
<211> LENGTH: 50
<212> TYPE: DNA
<213> ORGANISM: Artificial Sequence
<220> FEATURE:
<223> OTHER INFORMATION: oligo-178

<400> SEQUENCE: 13
acaggcgcta gcatatggca cagcatgacg aggcggggct cgcattagag                50

<210> SEQ ID NO 14
<211> LENGTH: 60
<212> TYPE: DNA
<213> ORGANISM: Artificial Sequence
<220> FEATURE:
<223> OTHER INFORMATION: oligo-170

<400> SEQUENCE: 14
gcggatccta ttattagcgc ggcgctaagg cccccgcaaa tttaatgttg atcgtatacc    60

<210> SEQ ID NO 15
<211> LENGTH: 43
<212> TYPE: DNA
```

```
<213> ORGANISM: Artificial Sequence
<220> FEATURE:
<223> OTHER INFORMATION: oligo-189

<400> SEQUENCE: 15
tttgcggggg ccttaccgag caagagcaaa aaaatcttaa agg                    43

<210> SEQ ID NO 16
<211> LENGTH: 37
<212> TYPE: DNA
<213> ORGANISM: Artificial Sequence
<220> FEATURE:
<223> OTHER INFORMATION: oligo-191

<400> SEQUENCE: 16
gcggatccta tttatttcttc tttttcggag cctgggc                          37

<210> SEQ ID NO 17
<211> LENGTH: 21
<212> TYPE: PRT
<213> ORGANISM: Artificial Sequence
<220> FEATURE:
<223> OTHER INFORMATION: Modified third alpha helix of immunoglobulin
      binding C domain of protein A

<400> SEQUENCE: 17

Pro Ser Lys Ser Lys Lys Ile Leu Lys Glu Ala Lys Lys Leu Asn Lys
1               5                   10                  15

Ala Gln Ala Pro Lys
            20

<210> SEQ ID NO 18
<211> LENGTH: 3
<212> TYPE: PRT
<213> ORGANISM: Artificial Sequence
<220> FEATURE:
<223> OTHER INFORMATION: Artificial sequence of C-terminal

<400> SEQUENCE: 18

Lys Lys Lys
1

<210> SEQ ID NO 19
<211> LENGTH: 69
<212> TYPE: DNA
<213> ORGANISM: Artificial Sequence
<220> FEATURE:
<223> OTHER INFORMATION: oligo-193

<400> SEQUENCE: 19
ggctcgcatt agagacgccg gaaccggagg aagaggtgac gatcaaggct aacctgatct    60
ttgcggatg                                                           69

<210> SEQ ID NO 20
<211> LENGTH: 67
<212> TYPE: DNA
<213> ORGANISM: Artificial Sequence
<220> FEATURE:
<223> OTHER INFORMATION: oligo-194

<400> SEQUENCE: 20
catcgctcac cgcctttgcg aaggtgcctt tgaattcagc gttctgggtg ctcccatccg    60
caaagat                                                             67
```

```
<210> SEQ ID NO 21
<211> LENGTH: 69
<212> TYPE: DNA
<213> ORGANISM: Artificial Sequence
<220> FEATURE:
<223> OTHER INFORMATION: oligo-195

<400> SEQUENCE: 21
cggtgagcga tgcctacgcg tatgcagatg cgctgaaaaa ggacaacggg gaatatacgg    60
tagacgtgg                                                            69

<210> SEQ ID NO 22
<211> LENGTH: 66
<212> TYPE: DNA
<213> ORGANISM: Artificial Sequence
<220> FEATURE:
<223> OTHER INFORMATION: oligo-196

<400> SEQUENCE: 22
gctcggtaag gcccccgcaa atttaatgtt cagcgtcagc cctttatccg ccacgtctac    60
cgtata                                                               66

<210> SEQ ID NO 23
<211> LENGTH: 54
<212> TYPE: DNA
<213> ORGANISM: Artificial Sequence
<220> FEATURE:
<223> OTHER INFORMATION: oligo-199

<400> SEQUENCE: 23
cggctgaatt caaaggcacc ttcgaagagg cgaccgcgaa ggcctacgcg tatg          54

<210> SEQ ID NO 24
<211> LENGTH: 30
<212> TYPE: DNA
<213> ORGANISM: Artificial Sequence
<220> FEATURE:
<223> OTHER INFORMATION: oligo-201

<400> SEQUENCE: 24
cttggcgagg aggtctgcat acgcgtaggc                                     30

<210> SEQ ID NO 25
<211> LENGTH: 63
<212> TYPE: DNA
<213> ORGANISM: Artificial Sequence
<220> FEATURE:
<223> OTHER INFORMATION: oligo-200

<400> SEQUENCE: 25
ctcctcgcca aggagaacgg ggaatatacg gccgatcttg aggatggcgg gaatacgatc    60
aac                                                                  63

<210> SEQ ID NO 26
<211> LENGTH: 32
<212> TYPE: DNA
<213> ORGANISM: Artificial Sequence
<220> FEATURE:
<223> OTHER INFORMATION: oligo-197

<400> SEQUENCE: 26
ggctcgcatt agagacgccg gaagaaccga ag                                  32

<210> SEQ ID NO 27
```

```
<211> LENGTH: 34
<212> TYPE: DNA
<213> ORGANISM: Artificial Sequence
<220> FEATURE:
<223> OTHER INFORMATION: oligo-198

<400> SEQUENCE: 27
ttgaattcag ccgtctggat cttcccatcc gcaa                                34

<210> SEQ ID NO 28
<211> LENGTH: 30
<212> TYPE: DNA
<213> ORGANISM: Artificial Sequence
<220> FEATURE:
<223> OTHER INFORMATION: oligo-202

<400> SEQUENCE: 28
cttggcgagg aggtttgcat acgcgtaggc                                     30

<210> SEQ ID NO 29
<211> LENGTH: 48
<212> TYPE: DNA
<213> ORGANISM: Artificial Sequence
<220> FEATURE:
<223> OTHER INFORMATION: oligo-203

<400> SEQUENCE: 29
aaagatcagg ttaacgcgga tcgtcacttc ctcgcgcggt tcttccgg                 48

<210> SEQ ID NO 30
<211> LENGTH: 60
<212> TYPE: DNA
<213> ORGANISM: Artificial Sequence
<220> FEATURE:
<223> OTHER INFORMATION: oligo-204

<400> SEQUENCE: 30
gttaacctga tctttgcgga tgggcgcacc cagacggctg aattccgtgg caccttcgaa    60

<210> SEQ ID NO 31
<211> LENGTH: 30
<212> TYPE: DNA
<213> ORGANISM: Artificial Sequence
<220> FEATURE:
<223> OTHER INFORMATION: oligo-205

<400> SEQUENCE: 31
atattccccg ttcacgcggg cgaggagatc                                     30

<210> SEQ ID NO 32
<211> LENGTH: 30
<212> TYPE: DNA
<213> ORGANISM: Artificial Sequence
<220> FEATURE:
<223> OTHER INFORMATION: oligo-206

<400> SEQUENCE: 32
gcagatctcc tcgcccgcgt gaacggggaa                                     30

<210> SEQ ID NO 33
<211> LENGTH: 30
<212> TYPE: DNA
<213> ORGANISM: Artificial Sequence
<220> FEATURE:
<223> OTHER INFORMATION: oligo-207

<400> SEQUENCE: 33
```
aggcccccgc aaagcgaatg ttgatcgtat                                    30

<210> SEQ ID NO 34
<211> LENGTH: 40
<212> TYPE: DNA
<213> ORGANISM: Artificial Sequence
<220> FEATURE:
<223> OTHER INFORMATION: oligo-210

<400> SEQUENCE: 34
acaggcgcta gcatatgggg ccttagagac gccggaagaa                         40

<210> SEQ ID NO 35
<211> LENGTH: 30
<212> TYPE: DNA
<213> ORGANISM: Artificial Sequence
<220> FEATURE:
<223> OTHER INFORMATION: oligo-211

<400> SEQUENCE: 35
tcttgctcgg taaggccccg gcaaagcgaa                                    30

<210> SEQ ID NO 36
<211> LENGTH: 322
<212> TYPE: PRT
<213> ORGANISM: Artificial Sequence
<220> FEATURE:
<223> OTHER INFORMATION: Amino acid sequence of PL-424

<400> SEQUENCE: 36

Ala Gln His Asp Glu Ala Gly Leu Ala Leu Glu Thr Pro Glu Glu Pro
1               5                   10                  15

Arg Glu Glu Val Thr Ile Arg Val Asn Leu Ile Phe Ala Asp Gly Arg
            20                  25                  30

Thr Gln Thr Ala Glu Phe Arg Gly Thr Phe Glu Glu Ala Thr Ala Glu
        35                  40                  45

Ala Tyr Arg Tyr Ala Asp Leu Leu Ala Arg Val Asn Gly Glu Tyr Thr
    50                  55                  60

Ala Asp Leu Glu Asp Gly Gly Tyr Thr Ile Asn Ile Arg Phe Ala Gly
65                  70                  75                  80

Ala Leu Glu Thr Pro Glu Glu Pro Arg Glu Glu Val Thr Ile Arg Val
                85                  90                  95

Asn Leu Ile Phe Ala Asp Gly Arg Thr Gln Thr Ala Glu Phe Arg Gly
            100                 105                 110

Thr Phe Glu Glu Ala Thr Ala Glu Ala Tyr Arg Tyr Ala Asp Leu Leu
        115                 120                 125

Ala Arg Val Asn Gly Glu Tyr Thr Ala Asp Leu Glu Asp Gly Gly Tyr
    130                 135                 140

Thr Ile Asn Ile Arg Phe Ala Gly Ala Leu Glu Thr Pro Glu Glu Pro
145                 150                 155                 160

Arg Glu Glu Val Thr Ile Arg Val Asn Leu Ile Phe Ala Asp Gly Arg
                165                 170                 175

Thr Gln Thr Ala Glu Phe Arg Gly Thr Phe Glu Glu Ala Thr Ala Glu
            180                 185                 190

Ala Tyr Arg Tyr Ala Asp Leu Leu Ala Arg Val Asn Gly Glu Tyr Thr
        195                 200                 205

Ala Asp Leu Glu Asp Gly Gly Tyr Thr Ile Asn Ile Arg Phe Ala Gly
    210                 215                 220

```
Ala Leu Glu Thr Pro Glu Glu Pro Arg Glu Val Thr Ile Arg Val
225                 230                 235                 240

Asn Leu Ile Phe Ala Asp Gly Arg Thr Gln Thr Ala Glu Phe Arg Gly
                245                 250                 255

Thr Phe Glu Glu Ala Thr Ala Glu Ala Tyr Arg Tyr Ala Asp Leu Leu
                260                 265                 270

Ala Arg Val Asn Gly Glu Tyr Thr Ala Asp Leu Glu Asp Gly Gly Tyr
            275                 280                 285

Thr Ile Asn Ile Arg Phe Ala Gly Ala Leu Pro Ser Lys Ser Lys Lys
        290                 295                 300

Ile Leu Lys Glu Ala Lys Lys Leu Asn Lys Ala Gln Ala Pro Lys Lys
305                 310                 315                 320

Lys Lys

<210> SEQ ID NO 37
<211> LENGTH: 466
<212> TYPE: PRT
<213> ORGANISM: Artificial Sequence
<220> FEATURE:
<223> OTHER INFORMATION: Amino acid sequence of PL-624

<400> SEQUENCE: 37

Ala Gln His Asp Glu Ala Gly Leu Ala Leu Glu Thr Pro Glu Glu Pro
1               5                   10                  15

Arg Glu Glu Val Thr Ile Arg Val Asn Leu Ile Phe Ala Asp Gly Arg
                20                  25                  30

Thr Gln Thr Ala Glu Phe Arg Gly Thr Phe Glu Glu Ala Thr Ala Glu
            35                  40                  45

Ala Tyr Arg Tyr Ala Asp Leu Leu Ala Arg Val Asn Gly Glu Tyr Thr
50                  55                  60

Ala Asp Leu Glu Asp Gly Gly Tyr Thr Ile Asn Ile Arg Phe Ala Gly
65                  70                  75                  80

Ala Leu Glu Thr Pro Glu Glu Pro Arg Glu Val Thr Ile Arg Val
                85                  90                  95

Asn Leu Ile Phe Ala Asp Gly Arg Thr Gln Thr Ala Glu Phe Arg Gly
                100                 105                 110

Thr Phe Glu Glu Ala Thr Ala Glu Ala Tyr Arg Tyr Ala Asp Leu Leu
            115                 120                 125

Ala Arg Val Asn Gly Glu Tyr Thr Ala Asp Leu Glu Asp Gly Gly Tyr
        130                 135                 140

Thr Ile Asn Ile Arg Phe Ala Gly Ala Leu Glu Thr Pro Glu Glu Pro
145                 150                 155                 160

Arg Glu Glu Val Thr Ile Arg Val Asn Leu Ile Phe Ala Asp Gly Arg
                165                 170                 175

Thr Gln Thr Ala Glu Phe Arg Gly Thr Phe Glu Glu Ala Thr Ala Glu
            180                 185                 190

Ala Tyr Arg Tyr Ala Asp Leu Leu Ala Arg Val Asn Gly Glu Tyr Thr
        195                 200                 205

Ala Asp Leu Glu Asp Gly Gly Tyr Thr Ile Asn Ile Arg Phe Ala Gly
        210                 215                 220

Ala Leu Glu Thr Pro Glu Glu Pro Arg Glu Val Thr Ile Arg Val
225                 230                 235                 240

Asn Leu Ile Phe Ala Asp Gly Arg Thr Gln Thr Ala Glu Phe Arg Gly
                245                 250                 255

Thr Phe Glu Glu Ala Thr Ala Glu Ala Tyr Arg Tyr Ala Asp Leu Leu
```

```
                260                 265                 270
Ala Arg Val Asn Gly Glu Tyr Thr Ala Asp Leu Glu Asp Gly Gly Tyr
            275                 280                 285

Thr Ile Asn Ile Arg Phe Ala Gly Ala Leu Glu Thr Pro Glu Glu Pro
            290                 295                 300

Arg Glu Glu Val Thr Ile Arg Val Asn Leu Ile Phe Ala Asp Gly Arg
305                 310                 315                 320

Thr Gln Thr Ala Glu Phe Arg Gly Thr Phe Glu Glu Ala Thr Ala Glu
                325                 330                 335

Ala Tyr Arg Tyr Ala Asp Leu Leu Ala Arg Val Asn Gly Glu Tyr Thr
            340                 345                 350

Ala Asp Leu Glu Asp Gly Gly Tyr Thr Ile Asn Ile Arg Phe Ala Gly
            355                 360                 365

Ala Leu Glu Thr Pro Glu Glu Pro Arg Glu Glu Val Thr Ile Arg Val
            370                 375                 380

Asn Leu Ile Phe Ala Asp Gly Arg Thr Gln Thr Ala Glu Phe Arg Gly
385                 390                 395                 400

Thr Phe Glu Glu Ala Thr Ala Glu Ala Tyr Arg Tyr Ala Asp Leu Leu
                405                 410                 415

Ala Arg Val Asn Gly Glu Tyr Thr Ala Asp Leu Glu Asp Gly Gly Tyr
            420                 425                 430

Thr Ile Asn Ile Arg Phe Ala Gly Ala Leu Pro Ser Lys Ser Lys Lys
            435                 440                 445

Ile Leu Lys Glu Ala Lys Lys Leu Asn Lys Ala Gln Ala Pro Lys Lys
450                 455                 460

Lys Lys
465

<210> SEQ ID NO 38
<211> LENGTH: 30
<212> TYPE: DNA
<213> ORGANISM: Artificial Sequence
<220> FEATURE:
<223> OTHER INFORMATION: oligo-334

<400> SEQUENCE: 38
gaattcagcc gtctggatgc gcccatccgc                                    30

<210> SEQ ID NO 39
<211> LENGTH: 29
<212> TYPE: DNA
<213> ORGANISM: Artificial Sequence
<220> FEATURE:
<223> OTHER INFORMATION: oligo-335

<400> SEQUENCE: 39
ccagacggct gaattccgtg gcaccttcg                                     29
```

IMMUNOGLOBULIN-BINDING POLYPEPTIDE

TECHNICAL FIELD

The present invention relates to a polypeptide that binds to an immunoglobulin or a fragment thereof. More specifically, the present invention relates to a polypeptide having a high binding affinity for an immunoglobulin or a kappa chain fragment thereof, and having excellent stability under alkaline conditions (alkali stability). Furthermore, the present invention relates to a method for producing the polypeptide, an immobilized product of the polypeptide, and a method for separating an immunoglobulin or a fragment thereof using the polypeptide.

REFERENCE TO SEQUENCE LISTING

This application incorporates by reference the sequence listing submitted as ASCII text filed via EFS-Web on Apr. 20, 2018. The Sequence Listing is provided as a file entitled "28123894_1.txt," created on Apr. 20, 2018, and which is approximately 28.9 kilobytes in size.

BACKGROUND ART

Conventionally, immunoglobulins (also referred to as antibodies), which have high binding specificities for target substances, have been extensively used as research reagents or clinical test reagents. In recent years, advances in genetic recombination technology have led to the establishment of technologies for producing human antibodies or humanized antibodies, and immunoglobulins have been put to practical use as antibody preparations in medical fields such as treatment of rheumatism and cancer.

Immunoglobulins are typically produced by animal cell culture, and affinity chromatography, which uses ligands having an immunoglobulin-binding capacity, is extensively used for the purification of immunoglobulins. Affinity chromatography used for the purification of immunoglobulins uses polypeptides such as Protein A, Protein L, and Protein G or immunoglobulin-binding domains thereof as ligands that specifically bind to the immunoglobulins.

Meanwhile, in recent years, there has been a demand for improved stability of ligands used for the purification of immunoglobulins. In particular, in the purification of immunoglobulins, an alkaline solution is used to, for example, inactivate viruses and the like, or clean a support having a ligand immobilized thereon, and one of important factors for a ligand used in the purification of immunoglobulins is to have high stability towards alkalis.

Conventionally, active research has been conducted on technologies for improving the alkali stability of Protein A. Patent Literature 1, for example, has reported that substitution of specific amino acids in the C domain of Protein A or specific amino acid residues in the Z domain of Protein A can impart an excellent immunoglobulin-binding capacity and excellent alkali stability to Protein A. Patent Literature 2 has reported that substitution of an asparagine residue of Protein A with another amino acid can impart alkali stability to Protein A.

As described above, various technologies for imparting alkali stability to Protein A have been reported; however, under the current circumstances, sufficient research has not been conducted on technologies for imparting alkali stability to Protein L.

Protein L, which is localized on the cell surface of *Peptostreptococcus magnus* (synonym: *Finegoldia magna*), is known to be able to specifically bind to immunoglobulin kappa chains. Protein L derived from *Peptostreptococcus magnus* 312 strain (Non Patent Literature 1) and Protein L derived from *Peptostreptococcus magnus* 3316 strain (Non Patent Literature 2 and Patent Literature 3) have been reported. It is known that Protein L derived from *Peptostreptococcus magnus* 3316 strain has four domains that bind to immunoglobulin kappa chains (Non Patent Literature 2 and Patent Literature 3), that these domains have amino acid sequences very similar to one another, and that each of these four domains independently exhibits a binding capacity for immunoglobulins. The amino acid sequences of the five kappa chain-binding domains from 312 strain are also very similar to the amino acid sequences of the domains from 3316 strain. However, it has never been clarified what kinds of modifications contribute to the alkali stability in the amino acid sequences of the domains of Protein L derived from *Peptostreptococcus magnus*.

CITATION LIST

Patent Literature

Patent Literature 1: WO 2007/097361
Patent Literature 2: WO 2000/023580
Patent Literature 3: U.S. Pat. No. 6,162,903 (2000)

Non Patent Literature

Non Patent Literature 1: W. Kastern et al., J. Biol. Chem. (1992) 267, 12820-12825
Non Patent Literature 2: J. P. Murphy et al., Mol. Microbiol. (1994) 12, 911-920

SUMMARY OF INVENTION

Technical Problem

An object of the present invention is to provide a polypeptide having a high binding capacity for an immunoglobulin kappa chain, and having excellent alkali stability, by modifying an amino acid sequence of an immunoglobulin-binding domain of Protein L derived from *Peptostreptococcus magnus*.

Solution to Problem

The inventor of the present invention conducted extensive research to solve the aforementioned problem, and found that a polypeptide having a high binding capacity for an immunoglobulin kappa chain, and having excellent alkali stability can be obtained by substituting specific lysine residues in an immunoglobulin-binding domain of Protein L derived from *Peptostreptococcus magnus* 3316 strain, with a basic amino acid or a hydroxyl group-containing amino acid. The present invention was completed as a result of further research based on the findings.

In summary, the present invention provides aspects of invention as itemized below:

Item 1. A polypeptide comprising at least one immunoglobulin-binding domain shown in any of (1-1) to (1-4), (2-1) to (2-4), and (3-1) to (3-4):

(1-1) an immunoglobulin-binding domain comprising an amino acid sequence wherein at least two or more sites selected from the group consisting of positions 7, 13, 22, and 29 in the amino acid sequence as set forth in SEQ ID NO: 1 are each substituted with a basic amino acid other than lysine or a hydroxyl group-containing amino acid;

(1-2) an immunoglobulin-binding domain comprising an amino acid sequence wherein at least two or more sites selected from the group consisting of positions 7, 13, 22, and 29 in the amino acid sequence as set forth in SEQ ID NO: 2 are each substituted with a basic amino acid other than lysine or a hydroxyl group-containing amino acid;

(1-3) an immunoglobulin-binding domain comprising an amino acid sequence wherein at least two or more sites selected from the group consisting of positions 7, 13, 22, and 29 in the amino acid sequence as set forth in SEQ ID NO: 3 are each substituted with a basic amino acid other than lysine or a hydroxyl group-containing amino acid;

(1-4) an immunoglobulin-binding domain comprising an amino acid sequence wherein at least two or more sites selected from the group consisting of positions 6, 12, 21, and 28 in the amino acid sequence as set forth in SEQ ID NO: 4 are each substituted with a basic amino acid other than lysine or a hydroxyl group-containing amino acid;

(2-1) an immunoglobulin-binding domain comprising an amino acid sequence wherein at least two amino acids selected from the group consisting of positions 7, 13, 22, and 29 in the amino acid sequence as set forth in SEQ ID NO: 1 are each substituted with a basic amino acid other than lysine or a hydroxyl group-containing amino acid, wherein one or a few amino acids other than the amino acid-substituted sites are substituted, added, inserted, or deleted, the immunoglobulin-binding domain having a binding capacity for an immunoglobulin, and having improved alkali stability as compared to the polypeptide consisting of the amino acid sequence as set forth in SEQ ID NO: 1;

(2-2) an immunoglobulin-binding domain comprising an amino acid sequence wherein at least two amino acids selected from the group consisting of positions 7, 13, 22, and 29 in the amino acid sequence as set forth in SEQ ID NO: 2 are each substituted with a basic amino acid other than lysine or a hydroxyl group-containing amino acid, wherein one or a few amino acids other than the amino acid-substituted sites are substituted, added, inserted, or deleted, the immunoglobulin-binding domain having a binding capacity for an immunoglobulin, and having improved alkali stability as compared to the polypeptide consisting of the amino acid sequence as set forth in SEQ ID NO: 1;

(2-3) an immunoglobulin-binding domain comprising an amino acid sequence wherein at least two amino acids selected from the group consisting of positions 7, 13, 22, and 29 in the amino acid sequence as set forth in SEQ ID NO: 3 are each substituted with a basic amino acid other than lysine or a hydroxyl group-containing amino acid, wherein one or a few amino acids other than the amino acid-substituted sites are substituted, added, inserted, or deleted, the immunoglobulin-binding domain having a binding capacity for an immunoglobulin, and having improved alkali stability as compared to the polypeptide consisting of the amino acid sequence as set forth in SEQ ID NO: 1;

(2-4) an immunoglobulin-binding domain comprising an amino acid sequence wherein at least two amino acids selected from the group consisting of positions 6, 12, 21, and 28 in the amino acid sequence as set forth in SEQ ID NO: 4 are each substituted with a basic amino acid other than lysine or a hydroxyl group-containing amino acid, wherein one or a few amino acids other than the amino acid-substituted sites are substituted, added, inserted, or deleted, the immunoglobulin-binding domain having a binding capacity for an immunoglobulin, and having improved alkali stability as compared to the polypeptide consisting of the amino acid sequence as set forth in SEQ ID NO: 1;

(3-1) an immunoglobulin-binding domain comprising an amino acid sequence wherein at least two amino acids selected from the group consisting of positions 7, 13, 22, and 29 in the amino acid sequence as set forth in SEQ ID NO: 1 are each substituted with a basic amino acid other than lysine or a hydroxyl group-containing amino acid, wherein an amino acid sequence excluding the amino acid-substituted sites has at least 80% sequence identity with the amino acid sequence as set forth in SEQ ID NO: 1, the immunoglobulin-binding domain having a binding capacity for an immunoglobulin, and having improved alkali stability as compared to the polypeptide consisting of the amino acid sequence as set forth in SEQ ID NO: 1;

(3-2) an immunoglobulin-binding domain comprising an amino acid sequence wherein at least two amino acids selected from the group consisting of positions 7, 13, 22, and 29 in the amino acid sequence as set forth in SEQ ID NO: 2 are each substituted with a basic amino acid other than lysine or a hydroxyl group-containing amino acid, wherein an amino acid sequence excluding the amino acid-substituted sites has at least 80% sequence identity with the amino acid sequence as set forth in SEQ ID NO: 2, the immunoglobulin-binding domain having a binding capacity for an immunoglobulin, and having improved alkali stability as compared to the polypeptide consisting of the amino acid sequence as set forth in SEQ ID NO: 2;

(3-3) an immunoglobulin-binding domain comprising an amino acid sequence wherein at least two amino acids selected from the group consisting of positions 7, 13, 22, and 29 in the amino acid sequence as set forth in SEQ ID NO: 3 are each substituted with a basic amino acid other than lysine or a hydroxyl group-containing amino acid, wherein an amino acid sequence excluding the amino acid-substituted sites has at least 80% sequence identity with the amino acid sequence as set forth in SEQ ID NO: 3, the immunoglobulin-binding domain having a binding capacity for an immunoglobulin, and having improved alkali stability as compared to the polypeptide consisting of the amino acid sequence as set forth in SEQ ID NO: 3; and (3-4) an immunoglobulin-binding domain comprising an amino acid sequence wherein at least two amino acids selected from the group consisting of positions 6, 12, 21, and 28 in the amino acid sequence as set forth in SEQ ID NO: 4 are each substituted with a basic amino acid other than lysine or a hydroxyl group-containing amino acid, wherein an amino acid sequence excluding the amino acid-substituted sites has at least 80% sequence identity with the amino acid sequence as set forth in SEQ ID NO: 4, the immunoglobulin-binding domain having a binding capacity for an immunoglobulin, and having improved alkali stability as compared to the polypeptide consisting of the amino acid sequence as set forth in SEQ ID NO: 4.

Item 2. The polypeptide according to item 1, which is a single domain peptide comprising one immunoglobulin-binding domain selected from the immunoglobulin-binding domains shown in (1-1) to (1-4), (2-1) to (2-4), and (3-1) to (3-4).

Item 3. The polypeptide according to item 1, which is a multidomain peptide wherein two or more immunoglobulin-binding domains selected from the immunoglobulin-binding domains shown in (1-1) to (1-4), (2-1) to (2-4), and (3-1) to (3-4) are linked.

Item 4. The polypeptide according to any one of items 1 to 3, which comprises at least any one of the immunoglobulin-binding domains shown in (1-1), (2-1), and (3-1), wherein all of positions 7, 13, 22, and 29 in the amino acid sequence as set forth in SEQ ID NO: 1 are each substituted with a basic amino acid or a hydroxyl group-containing amino acid.

Item 5. The polypeptide according to any one of items 1 to 4, which comprises at least any one of the immunoglobulin-binding domains shown in (1-1), (2-1), and (3-1),
wherein at least two or more sites selected from the group consisting of positions 7, 13, 22, and 29 in the amino acid sequence as set forth in SEQ ID NO: 1 are each substituted with arginine or threonine.

Item 6. The polypeptide according to any one of items 1 to 3, which comprises at least any one of the immunoglobulin-binding domains shown in (1-2), (2-2), and (3-2),
wherein all of positions 7, 13, 22, and 29 in the amino acid sequence as set forth in SEQ ID NO: 2 are each substituted with a basic amino acid or a hydroxyl group-containing amino acid.

Item 7. The polypeptide according to any one of items 1 to 3 and 6, which comprises at least any one of the immunoglobulin-binding domains shown in (1-2), (2-2), and (3-2),
wherein at least two or more sites selected from the group consisting of positions 7, 13, 22, and 29 in the amino acid sequence as set forth in SEQ ID NO: 2 are each substituted with arginine or threonine.

Item 8. The polypeptide according to any one of items 1 to 3, which comprises at least any one of the immunoglobulin-binding domains shown in (1-3), (2-3), and (3-3),
wherein all of positions 7, 13, 22, and 29 in the amino acid sequence as set forth in SEQ ID NO: 3 are each substituted with a basic amino acid or a hydroxyl group-containing amino acid.

Item 9. The polypeptide according to any one of items 1 to 3 and 8, which comprises at least any one of the immunoglobulin-binding domains shown in (1-3), (2-3), and (3-3),
wherein at least two or more sites selected from the group consisting of positions 7, 13, 22, and 29 in the amino acid sequence as set forth in SEQ ID NO: 3 are each substituted with arginine or threonine.

Item 10. The polypeptide according to any one of items 1 to 3, which comprises at least any one of the immunoglobulin-binding domains shown in (1-4), (2-4), and (3-4),
wherein all of positions 6, 12, 21, and 28 in the amino acid sequence as set forth in SEQ ID NO: 4 are each substituted with a basic amino acid or a hydroxyl group-containing amino acid.

Item 11. The polypeptide according to any one of items 1 to 3 and 10, which comprises at least any one of the immunoglobulin-binding domains shown in (1-4), (2-4), and (3-4),
wherein at least two or more sites selected from the group consisting of positions 6, 12, 21, and 28 in the amino acid sequence as set forth in SEQ ID NO: 4 are each substituted with arginine or threonine.

Item 12. DNA encoding the polypeptide according to any one of items 1 to 11.

Item 13. A recombinant vector comprising the DNA according to item 12.

Item 14. A transformant obtained by transforming a host with the recombinant vector according to item 13.

Item 15. A method for producing the polypeptide according to any one of items 1 to 11, comprising the step of culturing the transformant according to item 14.

Item 16. An immunoglobulin-binding support comprising the polypeptide according to any one of items 1 to 11 immobilized on an insoluble support.

Item 17. A method for separating an immunoglobulin or a fragment thereof, comprising separating an immunoglobulin or a kappa chain-containing fragment thereof, using the immunoglobulin-binding support according to item 16.

Advantageous Effects of Invention

The polypeptide of the present invention, which has a high binding capacity for an immunoglobulin or a kappa chain-containing fragment thereof, can maintain the binding capacity for an immunoglobulin or a kappa chain-containing fragment thereof even if it is subjected to alkaline conditions. Thus, even if the polypeptide of the present invention is repeatedly eluted or cleaned with an alkaline solution, a decrease in the binding capacity for an immunoglobulin or a kappa chain-containing fragment thereof can be inhibited, leading to reduced costs and increased efficiency for producing an immunoglobulin or a kappa chain-containing fragment thereof.

BRIEF DESCRIPTION OF DRAWINGS

FIG. 1 is a diagram that compares the amino acid sequences of immunoglobulin-binding domains 1 to 4 of Protein L derived from *Peptostreptococcus magunus* 3316 strain.

FIG. 2 is a diagram schematically illustrating a three-dimensional structure of immunoglobulin-binding domains 1 to 4 of Protein L derived from *Peptostreptococcus magunus* 3316 strain.

DESCRIPTION OF EMBODIMENTS

The present invention will be hereinafter described in detail. In sections other than SEQUENCE LISTING, the twenty amino acid residues in amino acid sequences may be shown as one-letter abbreviations. That is, G represents glycine (Gly), A represents alanine (Ala), V represents valine (Val), L represents leucine (Leu), I represents isoleucine (Ile), F represents phenylalanine (Phe), Y represents tyrosine (Tyr), W represents tryptophan (Trp), S represents serine (Ser), T represents threonine (Thr), C represents cysteine (Cys), M represents methionine (Met), D represents aspartic acid (Asp), E represents glutamic acid (Glu), N represents asparagine (Asn), Q represents glutamine (Gln), K represents lysine (Lys), R represents arginine (Arg), H represents histidine (His), and P represents proline (Pro).

As used herein, the term "non-polar amino acid" includes alanine, valine, leucine, isoleucine, proline, methionine, phenylalanine, and tryptophan. The term "uncharged amino acid" includes glycine, serine, threonine, cysteine, tyrosine, asparagine, and glutamine. The term "acidic amino acid" includes aspartic acid and glutamic acid. The term "basic amino acid" includes lysine, arginine, and histidine.

1. Polypeptide

Embodiments of the polypeptide of the present invention include a polypeptide comprising at least one immunoglobulin-binding domain shown in any of (1-1) to (1-4):

(1-1) an immunoglobulin-binding domain comprising an amino acid sequence wherein at least two or more sites selected from the group consisting of positions 7, 13, 22, and 29 in the amino acid sequence as set forth in SEQ ID NO:

1 are each substituted with a basic amino acid other than lysine or a hydroxyl group-containing amino acid;

(1-2) an immunoglobulin-binding domain comprising an amino acid sequence wherein at least two or more sites selected from the group consisting of positions 7, 13, 22, and 29 in the amino acid sequence as set forth in SEQ ID NO: 2 are each substituted with a basic amino acid other than lysine or a hydroxyl group-containing amino acid;

(1-3) an immunoglobulin-binding domain comprising an amino acid sequence wherein at least two or more sites selected from the group consisting of positions 7, 13, 22, and 29 in the amino acid sequence as set forth in SEQ ID NO: 3 are each substituted with a basic amino acid other than lysine or a hydroxyl group-containing amino acid; and (1-4) an immunoglobulin-binding domain comprising an amino acid sequence wherein at least two or more sites selected from the group consisting of positions 6, 12, 21, and 28 in the amino acid sequence as set forth in SEQ ID NO: 4 are each substituted with a basic amino acid other than lysine or a hydroxyl group-containing amino acid.

The amino acid sequences as set forth in SEQ ID NOS: 1 to 4 are the amino acid sequences of the four immunoglobulin-binding domains included in Protein L derived from *Peptostreptococcus magunus* 3316 strain (amino acid sequence as set forth in SEQ ID NO: 5, DDBJ database ID No. Q51918). Specifically, the amino acid sequence as set forth in SEQ ID NO: 1 corresponds to the immunoglobulin-binding domain present in a region from positions 468 to 537 in the amino acid sequence as set forth in SEQ ID NO: 5 (hereinafter sometimes denoted as "immunoglobulin-binding domain 4"). The amino acid sequence as set forth in SEQ ID NO: 2 corresponds to the immunoglobulin-binding domain present in a region from positions 394 to 463 in the amino acid sequence as set forth in SEQ ID NO: 5 (hereinafter sometimes denoted as "immunoglobulin-binding domain 3"). The amino acid sequence as set forth in SEQ ID NO: 3 corresponds to the immunoglobulin-binding domain present in a region from positions 320 to 389 in the amino acid sequence as set forth in SEQ ID NO: 5 (hereinafter sometimes denoted as "immunoglobulin-binding domain 2"). The amino acid sequence as set forth in SEQ ID NO: 4 corresponds to the immunoglobulin-binding domain present in a region from positions 249 to 317 in the amino acid sequence as set forth in SEQ ID NO: 5 (hereinafter sometimes denoted as "immunoglobulin-binding domain 1").

As shown in FIG. 1, immunoglobulin-binding domains 1 to 4 have highly conserved and highly homologous amino acid sequences.

As shown in FIG. 2, in each of immunoglobulin-binding domains 1 to 4, a β-sheet structure (positions 9 to 17 in the amino acid sequences as set forth in SEQ ID NOS: 1 to 3; positions 8 to 16 in the amino acid sequence as set forth in SEQ ID NO: 4) (hereinafter sometimes denoted as "β-sheet 1" or "β1"), a β-sheet structure (positions 23 to 30 in the amino acid sequences as set forth in SEQ ID NOS: 1 to 3; positions 22 to 29 in the amino acid sequence as set forth in SEQ ID NO: 4) (hereinafter sometimes denoted as "β-sheet 2" or "β2"), an α-helix structure (positions 32 to 50 in the amino acid sequences as set forth in SEQ ID NOS: 1 to 3; positions 31 to 49 in the amino acid sequence as set forth in SEQ ID NO: 4) (hereinafter sometimes denoted as "α-helix 1" or "α1"), a β-sheet structure (positions 53 to 58 in the amino acid sequences as set forth in SEQ ID NOS: 1 to 3; positions 52 to 57 in the amino acid sequence as set forth in SEQ ID NO: 4) (hereinafter sometimes denoted as "β-sheet 3" or "β3"), and a β-sheet structure (positions 63 to 68 in the amino acid sequences as set forth in SEQ ID NOS: 1 to 3; positions 62 to 67 in the amino acid sequence as set forth in SEQ ID NO: 4) (hereinafter sometimes denoted as "β-sheet 4" or "β4") are linked in order from the N-terminus. FIG. 2 shows, for convenience sake, a three-dimensional structure formed by immunoglobulin-binding domain 4 (SEQ ID NO: 1).

The amino acid at position 7 in each of the amino acid sequences as set forth in SEQ ID NOS: 1 to 3 and the amino acid at position 6 in the amino acid sequence as set forth in SEQ ID NO: 4 are present closer to the N-terminus than to β-sheet 1, and these amino acids are located at positions where they can readily interact with specific amino acids (the amino acid at position 33 in each of the amino acid sequences as set forth in SEQ ID NOS: 1 to 3; the amino acid at position 32 in the amino acid sequence as set forth in SEQ ID NO: 4) present in α-helix 1, because of the three-dimensional structure. Moreover, the amino acid at position 13 in each of the amino acid sequences as set forth in SEQ ID NOS: 1 to 3 and the amino acid at position 12 in the amino acid sequence as set forth in SEQ ID NO: 4 are present in β-sheet 1, and these amino acids are located at positions where they can readily interact with specific amino acids (the amino acid at position 27 in each of the amino acid sequences as set forth in SEQ ID NOS: 1 to 3; the amino acid at position 26 in the amino acid sequence as set forth in SEQ ID NO: 4) present in n-sheet 2, because of the three-dimensional structure. Moreover, the amino acid at position 22 in each of the amino acid sequences as set forth in SEQ ID NOS: 1 to 3 and the amino acid at position 21 in the amino acid sequence as set forth in SEQ ID NO: 4 are present in a loop region between β-sheet 1 and β-sheet 2, and these amino acids are located at positions where they can readily interact with specific amino acids (the amino acid at position 20 in each of the amino acid sequences as set forth in SEQ ID NOS: 1 to 3; the amino acid at position 19 in the amino acid sequence as set forth in SEQ ID NO: 4) present in the same loop region, because of the three-dimensional structure. Furthermore, the amino acid at position 29 in each of the amino acid sequences as set forth in SEQ ID NOS: 1 to 3 and the amino acid at position 28 in the amino acid sequence as set forth in SEQ ID NO: 4 are present in β-sheet 2, and these amino acids are located at positions where they can readily interact with specific amino acids (the amino acids at positions 8 and/or 11 in each of the amino acid sequences as set forth in SEQ ID NOS: 1 to 3; the amino acids at positions 7 and/or 10 in the amino acid sequence as set forth in SEQ ID NO: 4) present in β-sheet 1, because of the three-dimensional structure. These interactions are believed to be hydrogen bonds or electrostatic interactions.

In the polypeptide of the present invention, substitution of two or more sites of the specific four sites (positions 7, 13, 22, and 29 in each of the amino acid sequences as set forth in SEQ ID NOS: 1 to 3; positions 6, 12, 21, and 28 in the amino acid sequence as set forth in SEQ ID NO: 4) with specific amino acids in the amino acid sequence of each of these immunoglobulin-binding domains is believed to improve the structural stability by the interaction between the substituted amino acids and other amino acids located at positions where they can readily interact with them, thereby imparting improved alkali stability to the polypeptide.

In each of the immunoglobulin-binding domains shown in (1-1) to (1-3), the number of sites at which amino acid substitutions are to be introduced may be two or more of positions 7, 13, 22, and 29 in each of the amino acid sequences as set forth in SEQ ID NOS: 1 to 3; the number is preferably three or more, and more preferably four (i.e., all), from the viewpoint of further improving the alkali stability.

In each of the immunoglobulin-binding domains shown in (1-1) to (1-3), when amino acid substitutions are to be introduced at three of positions 7, 13, 22, and 29 in each of the amino acid sequences as set forth in SEQ ID NOS: 1 to 3, the sites at which amino acid substitutions are to be introduced may be selected as desired from these four sites; from the viewpoint of further improving the alkali stability, these sites are preferably the three sites of positions 13, 22, and 29, the three sites of positions 7, 22, and 29, or the three sites of positions 7, 13, and 22; and more preferably the three sites of positions 13, 22, and 29 or the three sites of positions 7, 22, and 29.

In each of the immunoglobulin-binding domains shown in (1-1) to (1-3), the amino acid substitutions to be introduced at two or more sites of positions 7, 13, 22, and 29 in each of the amino acid sequences as set forth in SEQ ID NOS: 1 to 3 may be substitutions with a basic amino acid other than lysine or a hydroxyl group-containing amino acid. Specific examples of substituting basic amino acids include arginine and histidine, with arginine being preferred, for example. Specific examples of substituting hydroxyl group-containing amino acids include threonine, serine, and tyrosine, with threonine being preferred, for example. From the viewpoint of further improving the alkali stability, examples of amino acid substitutions to be introduced at two or more sites of positions 7, 13, 22, and 29 include substitutions with arginine or threonine, with substitutions with arginine being preferred, for example.

In each of the immunoglobulin-binding domains shown in (1-1) to (1-3), when amino acid substitutions are to be introduced at two sites of positions 7, 13, 22, and 29 in each of the amino acid sequences as set forth in SEQ ID NOS: 1 to 3, the amino acid substitutions are preferably substitutions with a basic amino acid other than lysine for both the two sites, and more preferably substitutions with arginine for both the two sites. Moreover, in each of the immunoglobulin-binding domains shown in (1-1) to (1-3), when amino acid substitutions are to be introduced at three sites of positions 7, 13, 22, and 29 in each of the amino acid sequences as set forth in SEQ ID NOS: 1 to 3, the amino acid substitutions are preferably substitutions with a basic amino acid other than lysine (particularly arginine) for at least two sites, and more preferably substitutions with a basic amino acid other than lysine (particularly arginine) for all the three sites. Furthermore, in each of the immunoglobulin-binding domains shown in (1-1) to (1-3), when amino acid substitutions are to be introduced at the four sites of positions 7, 13, 22, and 29 in each of the amino acid sequences as set forth in SEQ ID NOS: 1 to 3, the amino acid substitutions are preferably substitutions with a basic amino acid other than lysine (particularly arginine) for at least two sites, more preferably substitutions with a basic amino acid other than lysine (particularly arginine) for at least three sites, and particularly preferably substitutions with a basic amino acid other than lysine (particularly arginine) for all the four sites.

Suitable examples of amino acid sequences of the immunoglobulin-binding domains shown in (1-1) to (1-3) include an amino acid sequence wherein the four sites of positions 7, 13, 22, and 29 in each of SEQ ID NOS: 1 to 3 are each substituted with a basic amino acid other than lysine (particularly arginine); an amino acid sequence wherein the three sites of positions 7, 22, and 29 in each of SEQ ID NOS: 1 to 3 are each substituted with a basic amino acid other than lysine (particularly arginine); and an amino acid sequence wherein the two sites of positions 7 and 13 in each of the amino acid sequences as set forth in SEQ ID NOS: 1 to 3 are each substituted with a basic amino acid other than lysine (particularly arginine), and the amino acid at position 22 is substituted with a basic amino acid other than lysine (particularly arginine or a histidine) or a hydroxyl group-containing amino acid (particularly threonine). Among the above, the amino acid sequence wherein the four sites of positions 7, 13, 22, and 29 in each of the amino acid sequences as set forth in SEQ ID NOS: 1 to 3 are each substituted with a basic amino acid other than lysine (particularly arginine) is particularly suitable in that it has outstanding alkali stability.

In the immunoglobulin-binding domain shown in (1-4), the number of sites at which amino acid substitutions are to be introduced may be two or more of positions 6, 12, 21, and 28 in the amino acid sequence as set forth in SEQ ID NO: 4; the number is preferably three or more, and more preferably four (i.e., all), from the viewpoint of further improving the alkali stability.

In the immunoglobulin-binding domain shown in (1-4), when amino acid substitutions are to be introduced at three of positions 6, 12, 21, and 28 in the amino acid sequence as set forth in SEQ ID NO: 4, the sites at which amino acid substitutions are to be introduced may be selected as desired from these four sites; from the viewpoint of further improving the alkali stability, these sites are preferably the three sites of positions 12, 21, and 28, the three sites of positions 6, 21, and 28, or the three sites of positions 6, 12, and 21; and more preferably the three sites of positions 12, 21, and 28 or the three sites of positions 6, 21, and 28.

In the immunoglobulin-binding domain shown in (1-4), the amino acid substitutions to be introduced at two or more sites of positions 6, 12, 21, and 28 in the amino acid sequence as set forth in SEQ ID NO: 4 may be substitutions with a basic amino acid other than lysine or a hydroxyl group-containing amino acid. Specific examples of substituting basic amino acids or hydroxyl group-containing amino acids, preferred examples thereof, and the like are the same as described above for the immunoglobulin-binding domains shown in (1-1) to (1-3).

In the immunoglobulin-binding domain shown in (1-4), when amino acid substitutions are to be introduced at two sites of positions 6, 12, 21, and 28 in the amino acid sequence as set forth in SEQ ID NO: 4, the amino acid substitutions are preferably substitutions with a basic amino acid other than lysine for both the two sites, and more preferably substitutions with arginine for both the two sites. Moreover, in the immunoglobulin-binding domain shown in (1-4), when amino acid substitutions are to be introduced at three sites of positions 6, 12, 21, and 28 in the amino acid sequence as set forth in SEQ ID NO: 4, the amino acid substitutions are preferably substitutions with a basic amino acid other than lysine (particularly arginine) for at least two sites, and more preferably substitutions with a basic amino acid other than lysine (particularly arginine) for all the three sites. Furthermore, in the immunoglobulin-binding domain shown in (1-4), when amino acid substitutions are to be introduced at the four sites of positions 6, 12, 21, and 28 in the amino acid sequence as set forth in SEQ ID NO: 4, the amino acid substitutions are preferably substitutions with a basic amino acid other than lysine (particularly arginine) for at least two sites, more preferably substitutions with a basic amino acid other than lysine (particularly arginine) for at least three sites, and particularly preferably substitutions with a basic amino acid other than lysine (particularly arginine) for all the four sites.

Suitable examples of amino acid sequences of the immunoglobulin-binding domain shown in (1-4) include an amino acid sequence wherein the four sites of positions 6, 12, 21, and 28 in the amino acid sequence as set forth in SEQ ID NO: 4 are each substituted with a basic amino acid other than lysine (particularly arginine); an amino acid sequence wherein the three sites of positions 6, 12, and 21 in the amino acid sequence as set forth in SEQ ID NO: 4 are each substituted with a basic amino acid other than lysine (particularly arginine); and an amino acid sequence wherein the two sites of positions 6 and 12 in the amino acid sequence as set forth in SEQ ID NO: 4 are each substituted with a basic amino acid other than lysine (particularly arginine), and the amino acid at position 21 is substituted with a basic amino acid other than lysine (particularly arginine or a histidine) or a hydroxyl group-containing amino acid (particularly threonine). Among the above, the amino acid sequence wherein the four sites of positions 6, 12, 21, and 28 in the amino acid sequence as set forth in SEQ ID NO: 4 are each substituted with a basic amino acid other than lysine (particularly arginine) is particularly suitable in that it has outstanding alkali stability.

Other embodiments of the polypeptide of the present invention include a polypeptide comprising at least one immunoglobulin-binding domain shown in any of (2-1) to (2-4) and (3-1) to (3-4):

(2-1) an immunoglobulin-binding domain comprising an amino acid sequence wherein at least two amino acids selected from the group consisting of positions 7, 13, 22, and 29 in the amino acid sequence as set forth in SEQ ID NO: 1 are each substituted with a basic amino acid or a hydroxyl group-containing amino acid other than lysine, wherein one or a few amino acids other than the amino acid-substituted sites are substituted, added, inserted, or deleted, the immunoglobulin-binding domain having a binding capacity for an immunoglobulin, and having improved alkali stability as compared to the polypeptide consisting of the amino acid sequence as set forth in SEQ ID NO: 1;

(2-2) an immunoglobulin-binding domain comprising an amino acid sequence wherein at least two amino acids selected from the group consisting of positions 7, 13, 22, and 29 in the amino acid sequence as set forth in SEQ ID NO: 2 are each substituted with a basic amino acid other than lysine or a hydroxyl group-containing amino acid, wherein one or a few amino acids other than the amino acid-substituted sites are substituted, added, inserted, or deleted, the immunoglobulin-binding domain having a binding capacity for an immunoglobulin, and having improved alkali stability as compared to the polypeptide consisting of the amino acid sequence as set forth in SEQ ID NO: 1;

(2-3) an immunoglobulin-binding domain comprising an amino acid sequence wherein at least two amino acids selected from the group consisting of positions 7, 13, 22, and 29 in the amino acid sequence as set forth in SEQ ID NO: 3 are each substituted with a basic amino acid other than lysine or a hydroxyl group-containing amino acid, wherein one or a few amino acids other than the amino acid-substituted sites are substituted, added, inserted, or deleted, the immunoglobulin-binding domain having a binding capacity for an immunoglobulin, and having improved alkali stability as compared to the polypeptide consisting of the amino acid sequence as set forth in SEQ ID NO: 1;

(2-4) an immunoglobulin-binding domain comprising an amino acid sequence wherein at least two amino acids selected from the group consisting of positions 6, 12, 21, and 28 in the amino acid sequence as set forth in SEQ ID NO: 4 are each substituted with a basic amino acid other than lysine or a hydroxyl group-containing amino acid, wherein one or a few amino acids other than the amino acid-substituted sites are substituted, added, inserted, or deleted, the immunoglobulin-binding domain having a binding capacity for an immunoglobulin, and having improved alkali stability as compared to the polypeptide consisting of the amino acid sequence as set forth in SEQ ID NO: 1;

(3-1) an immunoglobulin-binding domain comprising an amino acid sequence wherein at least two amino acids selected from the group consisting of positions 7, 13, 22, and 29 in the amino acid sequence as set forth in SEQ ID NO: 1 are each substituted with a basic amino acid other than lysine or a hydroxyl group-containing amino acid, wherein an amino acid sequence excluding the amino acid-substituted sites has at least 80% sequence identity with the amino acid sequence as set forth in SEQ ID NO: 1, the immunoglobulin-binding domain having a binding capacity for an immunoglobulin, and having improved alkali stability as compared to the polypeptide consisting of the amino acid sequence as set forth in SEQ ID NO: 1;

(3-2) an immunoglobulin-binding domain comprising an amino acid sequence wherein at least two amino acids selected from the group consisting of positions 7, 13, 22, and 29 in the amino acid sequence as set forth in SEQ ID NO: 2 are each substituted with a basic amino acid other than lysine or a hydroxyl group-containing amino acid, wherein an amino acid sequence excluding the amino acid-substituted sites has at least 80% sequence identity with the amino acid sequence as set forth in SEQ ID NO: 2, the immunoglobulin-binding domain having a binding capacity for an immunoglobulin, and having improved alkali stability as compared to the polypeptide consisting of the amino acid sequence as set forth in SEQ ID NO: 2;

(3-3) an immunoglobulin-binding domain comprising an amino acid sequence wherein at least two amino acids selected from the group consisting of positions 7, 13, 22, and 29 in the amino acid sequence as set forth in SEQ ID NO: 3 are each substituted with a basic amino acid other than lysine or a hydroxyl group-containing amino acid, wherein an amino acid sequence excluding the amino acid-substituted sites has at least 80% sequence identity with the amino acid sequence as set forth in SEQ ID NO: 3, the immunoglobulin-binding domain having a binding capacity for an immunoglobulin, and having improved alkali stability as compared to the polypeptide consisting of the amino acid sequence as set forth in SEQ ID NO: 3; and (3-4) an immunoglobulin-binding domain comprising an amino acid sequence wherein at least two amino acids selected from the group consisting of positions 6, 12, 21, and 28 in the amino acid sequence as set forth in SEQ ID NO: 4 are each substituted with a basic amino acid other than lysine or a hydroxyl group-containing amino acid, wherein an amino acid sequence excluding the amino acid-substituted sites has at least 80% sequence identity with the amino acid sequence as set forth in SEQ ID NO: 4, the immunoglobulin-binding domain having a binding capacity for an immunoglobulin, and having improved alkali stability as compared to the polypeptide consisting of the amino acid sequence as set forth in SEQ ID NO: 4.

In the immunoglobulin-binding domains shown in (2-1) to (2-4) and (3-1) to (3-4), the amino acid sites other than positions 7, 13, 22, and 29 in each of the amino acid sequences as set forth in SEQ ID NOS: 1 to 3 and the amino acid sites other than positions 6, 12, 21, and 28 in the amino acid sequence as set forth in SEQ ID NO 4 are sometimes denoted as "optionally modified sites", hereinafter.

The immunoglobulin-binding domains shown in (2-1) and (3-1) are modified products of the immunoglobulin-binding domain shown in (1-1). The forms of the amino acid substitutions to be introduced at least two of the amino acids at positions 7, 13, 22, and 29 in the amino acid sequence as set forth in SEQ ID NO: 1, preferred amino acid-substituted sites, and the like are the same as described above for the immunoglobulin-binding domain shown in (1-1).

The immunoglobulin-binding domains shown in (2-2) and (3-2) are modified products of the immunoglobulin-binding domain shown in (1-2). The forms of the amino acid substitutions to be introduced at least two of the amino acids at positions 7, 13, 22, and 29 in the amino acid sequence as set forth in SEQ ID NO: 2, preferred amino acid-substituted sites, and the like are the same as described above for the immunoglobulin-binding domain shown in (1-2).

The immunoglobulin-binding domains shown in (2-3) and (3-3) are modified products of the immunoglobulin-binding domain shown in (1-3). The forms of the amino acid substitutions to be introduced at least two of the amino acids at positions 7, 13, 22, and 29 in the amino acid sequence as set forth in SEQ ID NO: 3, preferred amino acid-substituted sites, and the like are the same as described above for the immunoglobulin-binding domain shown in (1-3).

The immunoglobulin-binding domains shown in (2-4) and (3-4) are modified products of the immunoglobulin-binding domain shown in (1-4). The forms of the amino acid substitutions to be introduced at least two of the amino acids at positions 6, 12, 21, and 28 in the amino acid sequence as set forth in SEQ ID NO: 4, preferred amino acid-substituted sites, and the like are the same as described above for the immunoglobulin-binding domain shown in (1-4).

The amino acid modification(s) to be introduced at the optionally modified sites of each of the immunoglobulin-binding domains shown in (2-1) to (2-4) may include only one modification (for example, substitution) from substitution, addition, insertion, and deletion, or may include two or more modifications (for example, substitution and insertion). In each of the immunoglobulin-binding domains shown in (2-1) to (2-4), the number of the amino acids to be substituted, added, inserted, or deleted at the optionally modified sites may be one, or more than one or a few, and may, for example, be 1 to 13, preferably 1 to 6, 1 to 5, or 1 to 4, more preferably 1 to 3, and particularly preferably 1 or 2, or 1.

In each of the immunoglobulin-binding domains shown in (3-1) to (3-4), an amino acid sequence excluding the amino acid-substituted sites may have at least 80% sequence identity with each of the amino acid sequences as set forth in SEQ ID NOS: 1 to 4; the sequence identity is preferably at least 90%, more preferably at least 95%, and particularly preferably at least 99%.

As used herein, in each of the immunoglobulin-binding domains shown in (3-1) to (3-4), the sequence identity of the amino acid sequence excluding the amino acid-substituted sites with each of the amino acid sequences as set forth in SEQ ID NOS: 1 to 4 refers to the sequence identity calculated by extracting only the optionally modified sites from each of the amino acid sequences as set forth in SEQ ID NOS: 1 to 4, and comparing only the optionally modified sites with the amino acid sequence. Moreover, "sequence identity" represents a value of amino acid sequence identity obtained using bl2seq program (Tatiana A. Tatsusova, Thomas L. Madden, FEMS Microbiol. Lett., Vol. 174, p 247-250, 1999) in BLAST PACKAGE [sgi32 bit edition, Version 2.0.12; available from National Center for Biotechnology Information (NCBI)]. The parameters may be set as follows: Gap insertion Cost value: 11, Gap extension Cost value: 1.

In each of the immunoglobulin-binding domains shown in (2-1) to (2-3) and (3-1) to (3-3), the amino acids at positions 8, 11, 20, 27, and 33 in each of the amino acid sequences as set forth in SEQ ID NOS: 1 to 3 are believed to contribute to the improvement in alkali stability by interaction with the basic amino acids other than lysine or hydroxyl group-containing amino acids located in the amino acid-substituted sites; therefore, it is preferred that no substitutions or deletions be introduced at these sites. Similarly, in the immunoglobulin-binding domains shown in (2-4) and (3-4), the amino acids at positions 7, 10, 19, 26, and 32 in the amino acid sequence as set forth in SEQ ID NO: 4 are believed to contribute to the improvement in alkali stability by interaction with the basic amino acids other than lysine or hydroxyl group-containing amino acids located in the amino acid-substituted sites; therefore, it is preferred that no substitutions or deletions be introduced at these sites.

Specific forms of the amino acid substitutions to be introduced at the optionally modified sites of each of the immunoglobulin-binding domains shown in (2-1) to (2-3) and (3-1) to (3-3) include substitution of the amino acid at position 2 with a lysine, substitution of the amino acid at position 48 with arginine, and substitution of the amino acid at position 67 with arginine, in each of the amino acid sequences as set forth in SEQ ID NOS: 1 to 3. Similarly, specific forms of the amino acid substitutions to be introduced at the optionally modified sites of each of the immunoglobulin-binding domains shown in (2-4) and (3-4) include substitution of the amino acid at position 2 with lysine, substitution of the amino acid at position 47 with arginine, and substitution of the amino acid at position 66 with arginine, in the amino acid sequence as set forth in SEQ ID NO: 4.

Other forms of the amino acid substitutions to be introduced at the optionally modified sites of each of the immunoglobulin-binding domains shown in (2-1) to (2-4) and (3-1) to (3-4) include conservative substitutions. That is, examples of such substitutions at the optionally modified sites include substitution of an amino acid before substitution that is a non-polar amino acid with another non-polar amino acid; substitution of an amino acid before substitution that is an uncharged amino acid with another uncharged amino acid; substitution of an amino acid before substitution that is an acidic amino acid with another acidic amino acid; and substitution of an amino acid before substitution that is a basic amino acid with another basic amino acid.

With regard to the immunoglobulin-binding domain shown in (2-1), the phrase "having a binding capacity for an immunoglobulin, and having improved alkali stability as compared to the polypeptide consisting of the amino acid sequence as set forth in SEQ ID NO: 1" means that the immunoglobulin-binding domain has a binding capacity for an immunoglobulin kappa chain, and the residual activity of the polypeptide immobilized on an agarose gel support, as measured under the below-described conditions, is higher than the residual activity of the polypeptide consisting of the amino acid sequence as set forth in SEQ ID NO: 1 measured under the same conditions. More specifically, the phrase means that the residual activity of the polypeptide measured under the below-described conditions is at least 1.8% higher, preferably at least 8% higher, and more preferably at least 18% higher than the residual activity of the polypeptide consisting of the amino acid sequence as set forth in SEQ ID NO: 1 measured under the same conditions. The same applies to the immunoglobulin-binding domains shown in (2-2) to (2-4) and (3-1) to (3-4).

Measurement Conditions

A polypeptide immobilized on an agarose gel support is cleaned with an aqueous solution of 0.1 M NaOH three times and replaced with the same alkaline solution, and then incubated at 25° C. for 17 hours (alkali treatment). Next, the polypeptide is washed with PBS three times, and then the amount of bound human IgG (mg/ml gel) is measured. Similarly, for a polypeptide immobilized on an agarose gel support that has not been subjected to the alkali treatment, the amount of bound human IgG (mg/ml gel) is measured. Using the amount of human IgG bound to the polypeptide that has not been subjected to the alkali treatment as 100%, the ratio of the amount of human IgG bound to the polypeptide after the alkali treatment is calculated as the residual activity (%).

Among the immunoglobulin-binding domains shown in (1-1) to (1-4), (2-1) to (2-4), and (3-1) to (3-4), the immunoglobulin-binding domains shown in (1-1), (2-1), and (3-1) are markedly superior in binding capacity for an immunoglobulin and alkali stability, and thus, are particularly suitable as the immunoglobulin-binding domains to be included in the polypeptide of the present invention.

The polypeptide of the present invention may be a single domain polypeptide having one immunoglobulin-binding domain, or may be a multidomain polypeptide in which two or more immunoglobulin-binding domains are linked. When the polypeptide of the present invention is a multidomain polypeptide, the polypeptide has the advantage of having an increased binding capacity for a kappa chain-containing fragment of an immunoglobulin.

When the polypeptide of the present invention is a single domain polypeptide, the polypeptide may contain one of the immunoglobulin-binding domains shown in (1-1) to (1-4), (2-1) to (2-4), and (3-1) to (3-4).

When the polypeptide of the present invention is a multidomain polypeptide, the polypeptide may contain at least one of the immunoglobulin-binding domains shown in (1-1) to (1-4), (2-1) to (2-4), and (3-1) to (3-4), or may contain two or more domains of the immunoglobulin-binding domains shown in (1-1) to (1-4), (2-1) to (2-4), and (3-1) to (3-4), or may contain one or more domains of the immunoglobulin-binding domains shown in (1-1) to (1-4), (2-1) to (2-4), and (3-1) to (3-4), as well as one or more of wild-type immunoglobulin-binding domains constituting Protein L (amino acid sequences as set forth in SEQ ID NOS: 1 to 4) and immunoglobulin-binding domains constituting Protein A. When the polypeptide of the present invention is a multidomain polypeptide, the polypeptide is preferably one in which all the immunoglobulin-binding domains constituting the polypeptide are any of the immunoglobulin-binding domains shown in (1-1) to (1-4), (2-1) to (2-4), and (3-1) to (3-4), from the viewpoint of imparting further improved alkali stability to the polypeptide.

When the polypeptide of the present invention is a multidomain polypeptide, the total number of linked immunoglobulin-binding domains may be 2 or more, preferably 2 to 10, and more preferably 2 to 6.

When the polypeptide of the present invention is a multidomain polypeptide, the individual immunoglobulin-binding domains constituting the polypeptide may be linked to one another directly between the C-terminus of one domain and the N-terminus of another, or may be linked to one another via 1 to 40, preferably 1 to 10 amino acid residues.

The polypeptide of the present invention may also have a polypeptide having another function, a peptide tag, or the like added at the N- or C-terminus, in order to impart a binding affinity for the support, improve the expression of the polypeptide, or impart the ease of purification, for example. The number of the amino acids to be added to the N-terminus and/or C-terminus of the polypeptide of the present invention for these purposes is, for example, 1 to 400, preferably 1 to 100, and more preferably 1 to 30, although not particularly limited thereto.

2. DNA

DNA encoding the polypeptide of the present invention (hereinafter sometimes denoted as the "DNA of the present invention") may be obtained by, for example, acquiring DNA encoding an immunoglobulin-binding domain of interest by PCR or the like, using DNA encoding wild-type Protein L (SEQ ID NO: 5) as a template, and introducing mutations into the DNA to introduce the above-described amino acid substitutions. The DNA of the present invention may also be artificially synthesized using a gene synthesis method.

The DNA encoding wild-type Protein L derived from *Peptostreptococcus magunus* 3316 strain (SEQ ID NO: 5) is known to have the nucleotide sequence as set forth in SEQ ID NO: 6, and may be isolated from *Peptostreptococcus magunus* 3316 strain by a standard method using PCR. The DNA encoding wild-type Protein L derived from *Peptostreptococcus magunus* 3316 strain may also be artificially synthesized using a gene synthesis method.

Methods for introducing specific mutations into specific sites of a nucleotide sequence are known, and, for example, site-directed mutagenesis for DNA may be used. Specific examples of methods for converting bases in DNA include using commercial kits.

The nucleotide sequence of DNA having mutations introduced in the nucleotide sequence can be confirmed using a DNA sequencer. Once the nucleotide sequence is determined, DNA encoding the polypeptide can then be obtained by chemical synthesis, PCR using a cloned probe as a template, or hybridization using a DNA fragment having the nucleotide sequence as a probe.

Moreover, a mutant of the DNA encoding the peptide, which has an equivalent function to that of the unmutated DNA, may be synthesized by site-directed mutagenesis, for example. The introduction of a mutation into the DNA encoding the peptide may be accomplished using known methods such as the Kunkel method, the gapped duplex method, and the megaprimer PCR method.

Examples of the DNA of the present invention include the nucleotide sequence as set forth in SEQ ID NO: 7. The DNA consisting of the nucleotide sequence as set forth in SEQ ID NO: 7 is DNA encoding a polypeptide consisting of an amino acid sequence wherein positions 7, 13, 22, and 29 are substituted with arginine in the amino acid sequence as set forth in SEQ ID NO: 1.

The DNA of the present invention also encompasses DNA that encodes an immunoglobulin-binding domain that has a binding capacity for an immunoglobulin, and has improved alkali stability as compared to the polypeptide consisting of the amino acid sequence as set forth in SEQ ID NO: 1, and that hybridizes under stringent conditions to DNA comprising a nucleotide sequence complementary to DNA consisting of the nucleotide sequence as set forth in SEQ ID NO: 7.

As used herein, "under stringent conditions" refers to conditions under which DNA is incubated at 50 to 65° C. for 4 hours to overnight in 6×SSC (1×SSC refers to 0.15 M NaCl, 0.015 M sodium citrate, pH 7.0) containing 0.5% SDS, 5×Denhardt's [Denhardt's, 0.1% bovine serum albumin (BSA), 0.1% polyvinylpyrrolidone, 0.1% ficoll 400], and 100 µg/ml of salmon sperm DNA.

Hybridization under stringent conditions is specifically performed using the following method: A nylon membrane having a DNA library or a cDNA library immobilized thereon is prepared, and then blocked at 65° C. in a prehybridization solution containing 6×SSC, 0.5% SDS, 5×Denhardt's, and 100 µg/ml of salmon sperm DNA. Then, $^{32}$P-labeled probes are added, and the nylon membrane is incubated overnight at 65° C. The nylon membrane is washed in 6×SSC at room temperature for 10 minutes, in 2×SSC containing 0.1% SDS at room temperature for 10 minutes, and in 0.2×SSC containing 0.1% SDS at 45° C. for 30 minutes, and then an autoradiogram is taken to detect DNAs that specifically hybridize to the probes.

Furthermore, the DNA of the present invention also encompasses DNA that encodes an immunoglobulin-binding domain having a binding capacity for an immunoglobulin, and has improved alkali stability as compared to the polypeptide consisting of the amino acid sequence as set forth in SEQ ID NO: 1, and that has at least 80% homology with DNA consisting of the nucleotide sequence as set forth in SEQ ID NO: 7. The homology is preferably at least 90%, more preferably at least 95%, and particularly preferably at least 98%, for example.

As used herein, the DNA "homology" represents a value of identity obtained using bl2seq program (Tatiana A. Tatsusova, Thomas L. Madden, FEMS Microbiol. Lett., Vol. 174, p 247-250, 1999) in BLAST PACKAGE [sgi32 bit edition, Version 2.0.12; available from National Center for Biotechnology Information (NCBI)]. The parameters may be set as follows: Gap insertion Cost value: 11, Gap extension Cost value: 1.

In the DNA of the present invention, the frequency of codon usage is preferably optimized for a host. For example, when *Escherichia coli* is used as a host, DNA with a frequency of codon usage optimized for *Escherichia coli* is suitable.

3. Recombinant Vector

A recombinant vector comprising the DNA encoding the polypeptide of the present invention (hereinafter sometimes denoted as the "recombinant vector of the present invention") may be obtained by inserting the DNA of the present invention into an expression vector.

The recombinant vector of the present invention contains a regulatory factor such as a promoter operably linked to the DNA of the present invention. A representative example of a regulatory factor is a promoter; however, the recombinant vector of the present invention may further contain an enhancer or a transcription factor such as a CCAAT box, a TATA box, or an SPI site, as required. The phrase "operably linked" refers to the state in which the DNA of the present invention and any of various regulatory factors such as a promoter or an enhancer for regulating the DNA of the present invention are linked with each other in an operable manner in host cells.

A suitable expression vector is an expression vector constructed for genetic recombination from a phage, a plasmid, or a virus that can replicate autonomously in a host. Such expression vectors are known, and examples of commercially available expression vectors include pQE vectors (Qiagen), pDR540 and pRIT2T (GE Healthcare Bio-Sciences KK), and pET vectors (Merck Ltd.). The expression vector to be used may be selected to make an appropriate combination with host cells; for example, when *Escherichia coli* is used as host cells, preferred examples of combinations include the combination of a pET vector and *Escherichia coli* strain BL21 (DE3) and the combination of pDR540 vector and *Escherichia coli* strain JM109.

4. Transformant

A transformant is obtained by transforming a host with the recombinant vector of the present invention (hereinafter sometimes denoted as the "transformant of the present invention").

The host to be used for producing the transformant is not particularly limited so long as the recombinant vector is stable, and can replicate autonomously and express the phenotype of a foreign gene in the host. Examples of such hosts include bacteria such as the genus *Escherichia* including *Escherichia coli*, the genus *Bacillus* including *Bacillus subtilis*, and the genus *Pseudomonas* including *Pseudomonas putida*; and yeasts. Other examples of hosts include animal cells, insect cells, and plants. Among the above, *Escherichia coli* is particularly preferred.

The transformant of the present invention may be obtained by introducing the recombinant vector of the present invention into a host. The conditions under which the recombinant vector is introduced into the host may be determined as appropriate, in accordance with the type of the host, for example. When the host is a bacterium, examples of methods include electroporation and a method using competent cells obtained by calcium ion treatment. When the host is a yeast, examples of methods include electroporation, the spheroplast method, and the lithium acetate method. When the host is an animal cell, examples of methods include electroporation, the calcium phosphate method, and lipofection. When the host is an insect cell, examples of methods include the calcium phosphate method, lipofection, and electroporation. When the host is a plant, examples of methods include electroporation, the Agrobacterium method, the particle gun method, and the PEG method.

5. Production of Polypeptide

The polypeptide of the present invention can be produced by culturing the above-described transformant.

The conditions for culturing the transformant may be determined as appropriate, in consideration of the nutrition physiological properties of the host; preferred examples of culture methods include liquid culture. For industrial production, aeration-agitation culture is preferred.

The transformant of the present invention is cultured, and the culture medium is subjected to a method such as centrifugation to collect the culture supernatant or cells. When the polypeptide of the present invention is accumulated in cells, the cells may be subjected to sonication, a mechanical method such as French press, or a treatment with a lytic enzyme such as lysozyme, and may then be solubilized, as required, with an enzyme such as protease or a surfactant such as sodium dodecyl sulfate (SDS) to obtain water-soluble fractions containing the polypeptide of the present invention.

Moreover, by appropriate selection of an expression vector and a host, the expressed polypeptide of the present invention may be secreted in culture medium.

The culture medium or water-soluble fractions containing the polypeptide of the present invention obtained as described above may be directly subjected to a purification treatment, or may be subjected to a purification treatment after concentrating the polypeptide of the present invention in the culture medium or water-soluble fractions.

The concentration may be accomplished by, for example, vacuum concentration, membrane concentration, salting-out, or fractional precipitation using a hydrophilic organic solvent (for example, methanol, ethanol, or acetone).

The purification treatment for the polypeptide of the present invention may be accomplished by using methods such as, for example, gel filtration, hydrophobic chromatography, ion-exchange chromatography, and affinity chromatography in an appropriate combination.

The polypeptide of the present invention thus purified may be formed into a powder, as required, by lyophilization, vacuum drying, spray drying, or the like.

6. Immunoglobulin-Binding Support

The polypeptide of the present invention is immobilized on an insoluble support and then used as an immunoglobulin-binding support to facilitate the collection or purification of immunoglobulins. Examples of the insoluble support to be used to immobilize the polypeptide of the present invention include, although not particularly limited to, naturally occurring polymer materials such as chitosan, dextran, cellulose, and agarose; synthetic organic materials such as vinyl alcohol, polyimide, and methacrylate; and inorganic materials such as glass and silica.

While the shape of the insoluble support is not particularly limited, the insoluble support may be in the form of any of a hollow fiber membrane, a monolith, or beads, for example. Among these shapes, beads are suitable because they typically have a relatively large surface area per volume, and are suited for use in producing an affinity support having a high immunoglobulin binding capacity.

The polypeptide of the present invention may be immobilized on an insoluble support by, for example, the coupling reaction of amino groups, carboxyl groups, or thiol groups in the polypeptide of the present invention with the insoluble support. Specifically, the immobilization may be accomplished by, for example, activating an insoluble support by reacting it with a coupling agent such as cyanogen bromide, epichlorohydrin, N-hydroxysuccinimide, tosyl chloride, tresyl chloride, carbodiimide, glutaraldehyde, or hydrazine, or introducing reactive functional groups such as carboxyl groups or thiol groups into the support, followed by the coupling reaction between the polypeptide of the present invention and the insoluble support. Such coupling reactions are well-known in the art (for example, Janson, J.-C., [Protein purification], 3rd edition, pages 221-258, ISBN 978-0-471-74661-4), and may be performed in accordance with a conventional method.

When the polypeptide of the present invention is immobilized on an insoluble support via amino groups in the polypeptide, it is preferred to use a support having reactive functional groups (such as tresyl groups, epoxy groups, carboxyl groups, or formyl groups) that can react with amino groups to form covalent bonds. Such insoluble supports are commercially available as TOYOPEARL AF-Tresyl-650, TOYOPEARL AF-Epoxy-650, TOYOPEARL AF-Carboxy-650, and TOYOPEARL AF-Formyl-650 (all from Tosoh Corporation); NHS-activated Sepharose, Cyanogen bromide-activated Sepharose, and Epoxy-activated Sepharose (all from GE Healthcare Bio-Sciences KK); Profinity Epoxide (Bio-Rad Inc.); Glyoxal-Agarose (from Agarose Beads Technologies); and Cellufine Formyl (JNC Corporation), and these commercially available products may be used.

Furthermore, the polypeptide of the present invention may be immobilized on an insoluble support by adding a condensation or cross-linking reagent such as carbodiimide or glutaraldehyde into a system in which the polypeptide of the present invention and the insoluble support co-exist.

7. Method for Separating Immunoglobulin or Fragment Thereof

The polypeptide of the present invention, which binds to immunoglobulin kappa chains, can be used to separate immunoglobulins such as IgG IgM, IgA, IgD, and IgE, as well as kappa chain-containing fragments (such as Fab fragments) thereof.

To separate an immunoglobulin or a fragment thereof using the polypeptide of the present invention, an insoluble support having the polypeptide of the present invention immobilized thereon may be used. Specifically, the separation of an immunoglobulin using an insoluble support having the polypeptide of the present invention immobilized thereon may be accomplished by affinity column chromatography.

The separation of an immunoglobulin by affinity column chromatography may be accomplished by passing a solution containing an immunoglobulin or a fragment thereof through a column packed with an insoluble support having the polypeptide of the present invention immobilized thereon, washing the inside of the column, and passing the eluting solution adjusted to an appropriate pH into the column to elute the immunoglobulin.

EXAMPLES

The present invention will be hereinafter specifically described with examples, although the present invention should not be interpreted as being limited to the following examples.

Referential Example 1

Production of Immunoglobulin-Binding Domain Proteins of Protein L Derived from *Peptostreptococcus magnus*, and Evaluation of Binding Capacity and Alkali Stability

[Production of Immunoglobulin-Binding Domains]
[Design and Construction of Modified Products]
A chimeric protein containing immunoglobulin-binding domain 1 was designated as PL-021, a chimeric protein containing immunoglobulin-binding domain 2 was designated as PL-022, a chimeric protein containing immunoglobulin-binding domain 3 was designated as PL-023, and a chimeric protein containing immunoglobulin-binding domain 4 was designated as PL-014.

[Preparation of PL-014 Expression Plasmid]
Initially, DNA fragment A1 (the first-half of immunoglobulin kappa light chain-binding domain 4) was prepared by PCR using synthetic oligo-DNAs oligo-166 (SEQ ID NO: 8) and oligo-167 (SEQ ID NO: 9) having about 15 bases at the 3' end complementary to each other, as templates for each other. Similarly, DNA fragment A2 (the latter-half of immunoglobulin kappa light chain-binding domain 4) was prepared by PCR using synthetic oligo-DNAs oligo-168 (SEQ ID NO: 10) and oligo-169 (SEQ ID NO: 11). Next, DNA fragment A1 and DNA fragment A2 were cleaved with restriction enzyme EcoRI, and ligated to each other by a ligation reaction to obtain DNA fragment A3. Next, DNA fragment A4 was prepared by PCR using DNA fragment A3 as a template, and using, as a forward primer, synthetic oligo-DNA oligo-178 (SEQ ID NO: 13) containing a translation initiation codon having NdeI recognition sequence and a sequence encoding an artificial N-terminal sequence "MAQHDEAGLAL" (SEQ ID NO: 12), and, as a reverse primer, synthetic oligo-DNA oligo-170 (SEQ ID NO: 14) containing EcoO109I recognition sequence in a sequence encoding an artificial sequence "NIKFAGAL". Separately, DNA fragment 5 encoding the third α-helix sequence of the immunoglobulin Fc-binding C-domain derived from modified Protein A disclosed in Patent Literature 1 (α-helix sequence consisting of 21 residues including eight lysines; SEQ ID NO: 17) and a subsequent sequence consisting of three lysine residues (SEQ ID NO: 18) was prepared by using, as a forward primer, synthetic oligo-DNA oligo-189 (SEQ ID NO: 15) containing EcoO109I recognition sequence in a sequence encoding an artificial sequence "FAGALPSKS", and, as a reverse primer, synthetic oligo-DNA oligo-191 (SEQ ID NO: 16) containing a sequence encoding an artificial C-terminal sequence "AQAPKKKK", followed by a translation stop codon and BamHI recognition sequence. DNA fragment A4 was cleaved with NdeI and EcoO109I, and DNA fragment 5 was cleaved with EcoO109I and BamHI, and the resulting fragments were simultaneously inserted into the NdeI-BamHI site of pET-9a plasmid (Novagen, Merck Ltd.) to obtain a chimeric protein PL-014 expression plasmid in which 11 residues of the artificial N-terminal sequence (SEQ ID NO: 12), 70 residues of immunoglobulin kappa light chain-binding domain 4 of Protein L (SEQ ID NO: 1), two residues of a linker sequence consisting of alanine-leucine, 21 residues of the modified C-terminal sequence of the third α-helix of the immunoglobulin Fc-binding C-domain derived from Protein A (SEQ ID NO: 17), and three residues of the artificial C-terminal sequence (SEQ ID NO: 18) were linked in this order from the N-terminus.

[Preparation of PL-021 Expression Plasmid]

As in the preparation of PL-014 expression plasmid, initially, DNA fragment B1 was prepared by PCR using synthetic oligo-DNAs oligo-193 (SEQ ID NO: 19) and oligo-194 (SEQ ID NO: 20) having about 15 bases at the 3' end complementary to each other, as templates for each other. Similarly, DNA fragment B2 was prepared by PCR using synthetic oligo-DNAs oligo-195 (SEQ ID NO: 21) and oligo-196 (SEQ ID NO: 22). Next, DNA fragment B3 was obtained by PCR using DNA fragment B1 and DNA fragment B2 as templates, and using synthetic oligo-DNAs oligo-178 (SEQ ID NO: 13) and oligo-196 (SEQ ID NO: 21) as primers. DNA fragment B3 was cleaved with NdeI and EcoO109I, and the resulting DNA fragment was inserted together with DNA fragment 5, which was cleaved with EcoO109I and BamHI, simultaneously into the NdeI-BamHI site of pET-9a plasmid to obtain a chimeric protein PL-021 expression plasmid in which 11 residues of the artificial N-terminal sequence (SEQ ID NO: 12), 69 residues of immunoglobulin kappa light chain-binding domain 1 of Protein L (SEQ ID NO: 4), two residues of a linker sequence consisting of alanine-leucine, 21 residues of the modified C-terminal sequence of the third α-helix of the immunoglobulin Fc-binding C-domain derived from Protein A (SEQ ID NO: 17), and three residues of the artificial C-terminal sequence (SEQ ID NO: 18) were linked in this order from the N-terminus.

[Preparation of PL-022 Expression Plasmid]

Since immunoglobulin kappa light chain-binding domain 2 of Protein L is identical to domain 4 in the sequence of 37 residues from the N-terminus, the previously prepared DNA fragment A1 was used as is. DNA fragment C2 was prepared by PCR using synthetic oligo-DNAs oligo-199 (SEQ ID NO: 23) and oligo-201 (SEQ ID NO: 24) having about 15 bases at the 3' end complementary to each other, as templates for each other. Next, DNA fragment A1 and fragment C2 were cleaved with restriction enzyme EcoRI, and ligated to each other by a ligation reaction to obtain DNA fragment C3. DNA fragment C4 was prepared by PCR using PL-014 expression plasmid as a template, and using synthetic oligo-DNAs oligo-200 (SEQ ID NO: 25) and oligo-191 (SEQ ID NO: 16) as primers. DNA fragment C3 and DNA fragment C4 were designed to have a partially overlapping sequence, and cDNA encoding PL-022 was obtained by PCR using these fragments as templates, and using synthetic oligo-DNAs oligo-178 (SEQ ID NO: 13) and oligo-191 (SEQ ID NO: 16) as primers. The resulting cDNA was cleaved with NdeI and BamHI, and then inserted into the NdeI-BamHI site of pET-9a plasmid to obtain a chimeric protein PL-022 expression plasmid in which 11 residues of the artificial N-terminal sequence (SEQ ID NO: 12), 70 residues of immunoglobulin kappa light chain-binding domain 2 of Protein L (SEQ ID NO: 3), two residues of a linker sequence consisting of alanine-leucine, 21 residues of the modified C-terminal sequence of the third α-helix of the immunoglobulin Fc-binding C-domain derived from Protein A (SEQ ID NO: 17), and three residues of the artificial C-terminal sequence (SEQ ID NO: 18) were linked in this order from the N-terminus.

[Preparation of PL-023 Expression Plasmid]

DNA fragment D1 was prepared by PCR using PL-014 expression plasmid as a template, and using synthetic oligo-DNAs oligo-197 (SEQ ID NO: 26) and oligo-198 (SEQ ID NO: 27) as primers. DNA fragment D2 was also prepared by PCR using synthetic oligo-DNAs oligo-199 (SEQ ID NO: 23) and oligo-202 (SEQ ID NO: 28) having about 15 bases at the 3' end complementary to each other, as templates for each other. Next, DNA fragment D3 was prepared by PCR using DNA fragment D1 and DNA fragment D2 as templates, and using synthetic oligo-DNAs oligo-197 (SEQ ID NO: 26) and oligo-202 (SEQ ID NO: 28) as primers. Since immunoglobulin kappa light chain-binding domain 3 of Protein L is identical to domain 2 in the sequence of 26 residues from the C-terminus, the previously prepared DNA fragment C4 was used as is, and cDNA encoding PL-023 was obtained by PCR using DNA fragment D3 and DNA fragment C4 as templates, and using synthetic oligo-DNAs oligo-178 (SEQ ID NO: 13) and oligo-191 (SEQ ID NO: 16) as primers. The resulting cDNA was cleaved with NdeI and BamHI, and then inserted into the NdeI-BamHI site of pET-9a plasmid to obtain a chimeric protein PL-023 expression plasmid in which 11 residues of the artificial N-terminal sequence (SEQ ID NO: 12), 70 residues of immunoglobulin kappa light chain-binding domain 3 of Protein L (SEQ ID NO: 2), two residues of a linker sequence consisting of alanine-leucine, 21 residues of the modified C-terminal sequence of the third α-helix of the immunoglobulin Fc-binding C-domain derived from Protein A (SEQ ID NO: 17), and three residues of the artificial C-terminal sequence (SEQ ID NO: 18) were linked in this order from the N-terminus.

The nucleic acid sequence of each of the expression plasmids for the respective immunoglobulin-binding domains obtained as described above was analyzed with a CEQ 8000 DNA sequencer (Beckman Coulter, Inc.) to confirm that the sequence was as designed. Next, BL21 (DE3) competent cells (Merck Ltd.) were transformed with each of the expression plasmids to obtain a strain expressing each of the proteins.

Each of the *Escherichia coli* strains expressing the respective immunoglobulin-binding domains was seed-cultured for 12 hours in LB medium containing 25 mg/L of kanamycin and 2.0% glucose. The resulting seed culture medium was inoculated into 2×TY medium containing 25 mg/L of kanamycin and 0.8% glucose, and cultured at 37° C. for 16 hours to express an immunoglobulin-binding domain of interest. Then, the culture medium was centrifuged to collect *Escherichia coli* cells. Next, the collected *Escherichia coli* cells were suspended in 50 mM sodium phosphate buffer (pH 6.5), the suspension was sonicated to disrupt the *Escherichia coli* cells, and then the sonicated suspension was centrifuged to collect the immunoglobulin-binding domain of interest in the supernatant. Each of the resulting supernatants as a cell extract was subjected to sodium dodecyl sulfate-15% polyacrylamide gel electrophoresis (SDS-PAGE), which confirmed that the immunoglobulin-binding domain of interest was produced in the position of the corresponding molecular weight.

[Purification of Immunoglobulin-Binding Domains and Purity Assay]

The cell extract of each of the immunoglobulin-binding domains was adjusted to pH 6.0, and then applied to a cation exchanger SP-Sepharose Fast Flow (GE Healthcare KK) column. The column was washed with 20 mM phosphate buffer (pH 6.0), and then the protein was eluted from the column with a linear gradient of 0.5 M NaCl. SDS-PAGE of the eluate confirmed that the immunoglobulin-binding domain of interest was eluted between 0.1 to 0.2 M NaCl. Next, the eluate containing the immunoglobulin-binding domain was adjusted to pH 9, and then added to an anion exchanger GigaCap Q (Tosoh Corporation) column. The column was washed with 20 mM phosphate buffer (pH 7.8), and then the immunoglobulin-binding domain was separated and eluted with a linear gradient of 0.3 M NaCl. Each of the eluates was subjected to SDS-PAGE to determine the purity; the results confirmed that each of the immunoglobulin-binding domains was purified as a single band in the position of the theoretical molecular weight.

[Immobilization on Gel Support and Evaluation by Immunoglobulin Binding Capacity Measurement]

Each of the immunoglobulin-binding domains thus purified was immobilized on a formyl-activated agarose gel support at a concentration of 10 mg/mL gel, in accordance with a conventional method. The reaction solution after the immobilization was collected, and the immobilization efficiency was measured. As a result, all the immunoglobulin-binding domains showed an immobilization efficiency of 90% or more. The gel support after the immobilization reaction was washed with a PBS solution, and then a PBS solution containing 40 mg/mL of human IgG (available from the Chemo-Sero-Therapeutic Research Institute) was added and the mixture was shaken for 1 hour. Then, human IgG bound to the gel support was eluted from the gel support washed with PBS, using 0.1 M glycine hydrochloride buffer (pH 2.5). The eluate was subjected to measurement of absorbance at 280 nm with a spectrophotometer, and the amount of the bound immunoglobulin (IgG binding capacity) was determined based on a specific absorption coefficient of 13.8 (1 $g^{-1}$ $cm^{-1}$).

Table 1 shows the amount of immobilization on the gel and the IgG binding capacity for each of the immunoglobulin-binding domains. These results showed that domain 4 has the highest IgG binding capacity of the four domains of Protein L.

TABLE 1

| IgG Binding Capacity of Immunoglobulin-Binding Domain | | | |
|---|---|---|---|
| Domain name | Number | Amount of Immobilization mg/mL gel | IgG Binding Capacity mg/mL gel |
| Domain 1 | PL-021 | 9.6 | 45.3 |
| Domain 2 | PL-022 | 9.5 | 53.3 |
| Domain 3 | PL-023 | 9.4 | 52.2 |
| Domain 4 | PL-014 | 9.6 | 57.4 |

[Analysis of Intermolecular Interactions between Each Immunoglobulin-Binding Domain, and Human IgG and Human Fab]

Interactions between each of the immunoglobulin-binding domains in a solution, and human IgG and human Fab fragments were analyzed with an intermolecular interaction analyzer BLItz (Pall Corporation). Biotinylated human IgG was prepared with a biotinylation kit (EZ-Link Biotinylation Kit; Thermo Fisher Scientific Inc.). A streptavidin sensor chip and biotinylated IgG adjusted to 0.1 mg/mL with 20 mM MES buffer (pH 6.5) containing 0.1% BSA (bovine serum albumin) were incubated at room temperature for 60 minutes to prepare an IgG-immobilized chip. Then, the sensor chip washed with 20 mM MES buffer (pH 6.5) was added to 20 mM MES buffer (pH 6.5) containing 0.1% BSA, containing each of the purified immunoglobulin-binding domains PL-021, PL-022, PL-023, and PL-014 at a concentration of 1.6 µg/mL, and the amount of each of the bound immunoglobulin-binding domains after 50 seconds was measured. The results showed that the binding activity was high in the following order: PL-014>PL-023=PL-022>PL-021.

Next, Fab prepared by papain treatment of human IgG was biotinylated and then immobilized on a streptavidin sensor chip in the same manner. The amount of each of the bound immunoglobulin-binding domains was measured, and PL-014 of domain 4 showed the highest binding activity for Fab as well.

The foregoing results showed that immunoglobulin-binding domain 4 in the solution also exhibits the highest binding activity for an IgG kappa light chain.

[Evaluation of Stability of Immobilized Gel Supports under Alkaline pH Conditions]

Next, the four immunoglobulin-binding domain-immobilized gel supports were washed with an aqueous solution of 0.1 M NaOH three times and replaced with the same alkaline solution, and then incubated at 25° C. for 17 hours. Then, the immobilized gel supports were washed with PBS three times, and human IgG binding capacities were measured under the same conditions as described above. Using the amount of IgG bound to each support before the alkali treatment as 100%, the ratio of the amount of bound IgG remaining after 17 hours of the treatment was determined as the residual activity (%) after the alkali treatment. The results are shown in Table 2.

These results showed that the alkali stability was high in the following order: PL-014>PL-023>PL-022>PL-021. This revealed that domain 4 has the highest alkali stability of the four domains of Protein L. Hereinafter, the creation of modified products having even higher alkali stability was attempted using domain 4 as a basic design.

TABLE 2

Alkali Stability of Immunoglobulin-Binding Domain

| Domain name | Number | Amount of Immobilization mg/mL gel | Residual Activity (%) after Alkali Treatment |
|---|---|---|---|
| Domain 1 | PL-021 | 9.6 | 17.7 |
| Domain 2 | PL-022 | 9.5 | 39.1 |
| Domain 3 | PL-023 | 9.4 | 42.9 |
| Domain 4 | PL-014 | 9.6 | 64.1 |

Example 1

Production of Modified Products of Immunoglobulin-Binding Domain 4 and Evaluation of Binding Capacity and Alkali Stability

[Production of Modified Products]

With the aim of further improving the alkali stability, immunoglobulin-binding domain 4 having high immunoglobulin binding capacity and high alkali stability was used as a basic sequence to prepare modified products thereof having amino acid substitutions, with a focus on a total of eight amino acid residues, i.e., the threonine residue at position 2, and the seven lysine residues at positions 7, 13, 22, 29, 48, and 67, in immunoglobulin-binding domain 4.

[Design and Construction of Modified Products]

Domain 4 was used as a basic sequence to prepare modified products thereof, wherein the threonine residue at position 2, and the seven lysine residues at positions 7, 13, 22, 29, 48, and 67 shown in Table 3 were substituted.

[Preparation of PL-024 Expression Plasmid]

Initially, a modified product PL-024 expression plasmid was constructed wherein each of the lysine residues at the seven positions 7, 13, 22, 29, 48, and 67 was substituted with an arginine residue in the immunoglobulin-binding domain 4 region (SEQ ID NO: 1) present on the sequence of PL-014.

DNA fragment E1 was prepared by PCR using the PL-023 expression plasmid as a template, and using synthetic oligo-DNAs oligo-178 (SEQ ID NO: 13) and oligo-203 (SEQ ID NO: 29) as primers. DNA fragment E2 was prepared by PCR using the PL-014 expression plasmid as a template, and using synthetic oligo-DNAs oligo-204 (SEQ ID NO: 30) and oligo-205 (SEQ ID NO: 31) as primers. Similarly, DNA fragment E3 was prepared by PCR using the PL-014 expression plasmid as a template, and using synthetic oligo-DNAs oligo-206 (SEQ ID NO: 32) and oligo-207 (SEQ ID NO: 33) as primers. Next, DNA fragment E4, which was the first-half of PL-024, was prepared by PCR using DNA fragment E1 and DNA fragment E2 as templates, and using oligo-178 (SEQ ID NO: 13) and oligo-205 (SEQ ID NO: 31) as primers; and DNA fragment E5, which was the latter-half of PL-024, was prepared by PCR using fragment E3 and fragment 5 as templates, and using synthetic oligo-DNAs oligo-206 and oligo-191 as primers. Lastly, the entire cDNA fragment of PL-024 was prepared by PCR using DNA fragment E4 and DNA fragment E5 as templates, and using synthetic oligo-DNAs oligo-178 (SEQ ID NO: 13) and oligo-191 (SEQ ID NO: 16) as primers, and this cDNA was cleaved with NdeI and BamHI, and inserted into the NdeI-BamHI site of pET-9a plasmid to obtain a chimeric protein PL-024 expression plasmid.

[Preparation of Chimeric Protein Expression Plasmids Having Combinations of Substitutions of Eight Amino Acid Residues at Positions 2, 7, 13, 22, 29, 48, and 67]

Next, cDNAs encoding modified products having a plurality of combinations of substitutions of the amino acid residues at the eight positions 2, 7, 13, 22, 29, 48, and 67 in the immunoglobulin-binding domain 4 region (SEQ ID NO: 1) were prepared. Specifically, using the cDNA of PL-014 as a template, and using prepared oligo-DNAs having a mutated nucleotide sequence at each of the positions, initially, a cDNA fragment encoding one amino acid substitution at each of positions 2, 7, 13, 22, 29, 48, and 67 was prepared by an overlap extension method (two-step PCR method). Next, using the cDNA of one amino acid substitution as a template, a mutation was introduced at another position by the same overlap extension method (two-step PCR method). Furthermore, by PCR using the resulting modified product plasmid as a template, and using primers that produce a mutation at another position, cDNA fragments of modified products including amino acid substitutions at various combinations of a plurality of sites were prepared.

Each of the cDNAs of the modified products obtained as described above was inserted into the *Escherichia coli* expression vector pET9a as in Example 1 to construct an expression plasmid. Table 3 shows the substitution patterns of the obtained modified products.

TABLE 3

| | Modified Sites and Substituting Amino Acids in Amino Acid Sequence as Set Forth in SEQ ID NO: 1 | | | | | | |
|---|---|---|---|---|---|---|---|
| | Position 2 | Position 7 | Position 13 | Position 22 | Position 29 | Position 48 | Position 67 |
| Wild Type (PL-014) | T | K | K | K | K | K | K |
| Modified Products | | | | | | | |
| PL-024 | | R | R | R | R | R | R |
| PL-026 | K | R | R | | | | |
| PL-027 | | R | R | R | | | |
| PL-028 | K | | | | R | R | R |
| PL-035 | | R | R | | | | |

TABLE 3-continued

Modified Sites and Substituting Amino Acids in Amino Acid Sequence as Set Forth in SEQ ID NO: 1

| | Position 2 | Position 7 | Position 13 | Position 22 | Position 29 | Position 48 | Position 67 |
|---|---|---|---|---|---|---|---|
| PL-036 | K | R | R | R | | | |
| PL-038 | R | R | R | R | R | R | R |
| PL-043 | R | | | | | | |
| PL-044 | K | | | R | | | |
| PL-045 | R | | | R | | | |
| PL-046 | K | R | | R | | | |
| PL-047 | K | | R | R | | | |
| PL-048 | K | | R | R | R | | |
| PL-049 | K | R | R | R | R | | |
| PL-050 | K | R | R | T | | | |
| PL-051 | K | R | R | L | | | |
| PL-052 | K | R | R | H | | | |
| PL-053 | K | R | R | E | | | |
| PL-054 | K | R | R | Q | | | |
| PL-055 | K | R | R | F | | | |
| PL-056 | K | R | R | A | | | |
| PL-057 | K | R | R | | R | | |
| PL-058 | K | R | | R | R | | |
| PL-059 | K | R | | | R | | |
| PL-060 | K | T | R | R | | | |

In the table, the blank fields in the columns of amino acid sites for each of the modified products indicate that no mutations were introduced (i.e., T at position 2; K at positions 7, 13, 22, 29, 48, and 67).

The nucleic acid sequence of each of the expression plasmids thus obtained was analyzed with a CEQ 8000 DNA sequencer (Beckman Coulter, Inc.) to confirm that the sequence was as designed. Next, BL21 (DE3) competent cells (Merck Ltd.) were transformed with each of the expression plasmids to obtain a strain expressing each of the modified products of immunoglobulin-binding domain 4.

Each of the *Escherichia coli* strains expressing the respective modified products of immunoglobulin-binding domain 4 was cultured at 37° C. for 16 hours in the same manner as described in Referential Example 1 above to express the modified product of immunoglobulin-binding domain 4 of interest. Then, the culture medium was centrifuged to collect *Escherichia coli* cells. Next, the collected *Escherichia coli* cells were suspended in 50 mM sodium phosphate buffer (pH 6.5), the suspension was sonicated to disrupt the *Escherichia coli* cells, and then the sonicated suspension was centrifuged to collect the modified product of immunoglobulin-binding domain 4 of interest in the supernatant. Each of the resulting supernatants as a cell extract was subjected to SDS-PAGE, which confirmed that the modified product of immunoglobulin-binding domain 4 of interest was produced in the position of the corresponding molecular weight.

[Purification of Modified Products and Purity Assay]

The cell extract of each of the modified products was adjusted to pH 6.0, and then applied to a cation exchanger SP-Sepharose Fast Flow (GE Healthcare KK) column in the same manner as described in Referential Example 1. The column was washed with 20 mM phosphate buffer (pH 6.0), and then the protein was eluted with a linear gradient of 0.5 M NaCl. Elution fractions containing the modified product of interest were collected and adjusted to pH 9, and then added to an anion exchanger GigaCap Q (Tosoh Corporation) column. The column was washed with 20 mM phosphate buffer (pH 7.8), and then the modified product of interest was eluted with a linear gradient of 0.3 M NaCl. Each of the eluates was subjected to SDS-PAGE to determine the purity; the results confirmed that each of the modified products was purified as a single band in the position of the theoretical molecular weight.

[Immobilization on Gel Support and Evaluation by Immunoglobulin Binding Capacity Measurement]

Each of the modified products thus purified was immobilized on a formyl-activated agarose gel support at a concentration of 10 mg/mL gel, in accordance with a conventional method. The reaction solution after the immobilization was collected, and the immobilization efficiency was measured. As a result, all the modified products showed an immobilization efficiency of 95% or more. Next, the human IgG binding capacity of each of the immobilized gel supports was measured in the same manner as described in Referential Example 1.

The results are shown in Table 4. As a result, PL-024 and PL-038 in which all the seven lysine residues at positions 7, 13, 22, 29, 48, and 67 were substituted in the amino acid sequence as set forth in SEQ ID NO: 1 exhibited binding capacity 11% higher than that of PL-014. Substitution of positions 29, 48, and 67 with arginine in the amino acid sequence as set forth in SEQ ID NO: 1 resulted in a 5% increase in binding capacity. Furthermore, the binding capacity tended to increase as the number of substitutions of the lysine residues at positions 7, 13, 22, 29, 48, and 67 with arginine increased in the amino acid sequence as set forth in SEQ ID NO: 1.

TABLE 4

| | Modified Sites and Substituting Amino Acids in Amino Acid Sequence as Set Forth in SEQ ID NO: 1 | | | | | | | IgG Binding Capacity |
|---|---|---|---|---|---|---|---|---|
| | Position 2 | Position 7 | Position 13 | Position 22 | Position 29 | Position 48 | Position 67 | mg/mL gel |
| Wild-Type (PL-014) | T | K | K | K | K | K | K | 57.0 |
| Modified Products | | | | | | | | |
| PL-024 | | R | R | R | R | R | R | 63.4 |
| PL-026 | K | R | R | | | | | 57.8 |
| PL-027 | | R | R | R | | | | 58.6 |
| PL-028 | K | | | | R | R | R | 60.1 |
| PL-035 | | R | R | | | | | 56.9 |
| PL-036 | K | R | R | R | | | | 59.1 |
| PL-038 | R | R | R | R | R | R | R | 63.6 |
| PL-043 | R | | | | | | | 59.3 |
| PL-044 | K | | | R | | | | 58.9 |
| PL-045 | R | | | R | | | | 60.6 |
| PL-046 | K | R | | R | | | | 59.7 |
| PL-047 | K | | R | R | | | | 59.2 |
| PL-048 | K | | R | R | R | | | 57.9 |
| PL-049 | K | R | R | R | R | | | 59.7 |
| PL-050 | K | R | R | T | | | | 59.0 |
| PL-051 | K | R | R | L | | | | 57.3 |
| PL-052 | K | R | R | H | | | | 58.5 |
| PL-053 | K | R | R | E | | | | 55.9 |
| PL-054 | K | R | R | Q | | | | 58.4 |
| PL-055 | K | R | R | F | | | | 57.3 |
| PL-056 | K | R | R | A | | | | 61.6 |
| PL-057 | K | R | R | | R | | | 55.6 |
| PL-058 | K | R | | R | R | | | 58.6 |
| PL-059 | K | R | | | R | | | 56.1 |
| PL-060 | K | T | R | R | | | | 57.6 |

In the table, the blank fields in the columns of amino acid sites for each of the modified products indicate that no mutations were introduced (i.e., T at position 2; K at positions 7, 13, 22, 29, 48, and 67).

[Evaluation of Stability of Modified Products Immobilized on Gel Support under Alkaline Conditions]

The gel support having each of the modified products immobilized thereon was replaced with an aqueous solution of 0.1 M NaOH, and then incubated at 25° C. for 17 hours. Then, the gel support was washed with PBS three times, and the human IgG binding capacity was measured under the same conditions as described above. Using the amount of IgG bound to each support before the alkali treatment as 100%, the ratio of the amount of bound IgG remaining after 17 hours of the treatment was determined as the residual activity (%) after the alkali treatment. The results are shown in Table 5.

As can be seen from Table 5, substitution of the threonine residue at position 2 with lysine or arginine in the amino acid sequence as set forth in SEQ ID NO: 1 did not affect the alkali stability.

Moreover, the cases where all the lysine residues at positions 7, 13, 22, 29, 48, and 67 were substituted with arginine in the amino acid sequence as set forth in SEQ ID NO: 1 were found to achieve markedly high alkali stability (PL-024 and PL-038).

Furthermore, the case where the four lysine residues at positions 7, 13, 22, and 29 were substituted with arginine in the amino acid sequence as set forth in SEQ ID NO: 1 (PL-049) was found to achieve the highest alkali stability; and the cases where the three lysine residues at positions 7, 13, and 22 were substituted with arginine (PL-027 and PL-036), the case where the three lysine residues at positions 13, 22, and 29 were substituted with arginine (PL-048), the case where the three lysine residues at positions 7, 13, and 29 were substituted with arginine (PL-057), and the case where the three lysine residues at positions 7, 22, and 29 were substituted with arginine (PL-058) were also found to achieve excellent alkali stability. In addition, the cases where two of the lysine residues at positions 7, 13, 22, and 29 were substituted with arginine in the amino acid sequence as set forth in SEQ ID NO: 1 (PL-026, PL-035, PL-046, PL-047, and PL-059) were also found to achieve improved alkali stability as compared to that of the wild-type (PL-014). In contrast, the case where only one of the lysine residues at positions 7, 13, 22, and 29 was substituted in the amino acid sequence as set forth in SEQ ID NO: 1 (PL-044) was found to exhibit no improvement in alkali stability.

On the other hand, the case where the lysine residues at positions 7 and 13 were substituted with arginine, and the lysine residue at position 22 was substituted with threonine in the amino acid sequence as set forth in SEQ ID NO: 1 (PL-050) was found to achieve improved alkali stability. Similarly, the case where position 22 was substituted with histidine (PL-052) exhibited alkali stability comparable to that of the cases where no mutations were introduced at position 22, and position 22 was a lysine residue (PL-026 and PL-035); however, the case where the lysine residue at position 22 was substituted with leucine, glutamic acid, glutamine, phenylalanine, or alanine was found to exhibit decreased alkali stability. The foregoing results confirmed that the lysine residue at position 22 is preferably substituted with a basic amino acid or a hydroxyl group-containing amino acid.

In the three-dimensional structure (FIG. 2) of immunoglobulin-binding domain 4 (polypeptide consisting of the amino acid sequence as set forth in SEQ ID NO: 1), the lysine residue at position 7 is located at a position where it can readily interact with the glutamic acid residue at position 33 in α-helix structure 1. Thus, substitution of the lysine residue at position 7 with an amino acid that forms an ionic bond or a hydrogen bond with glutamic acid (i.e., a basic amino acid or a hydroxyl group-containing amino acid) is assumed to achieve improved alkali stability by the interaction between the amino acid and the glutamic acid residue at position 33.

The same also applies to the lysine residues at positions 13, 22, and 29 in the amino acid sequence as set forth in SEQ ID NO: 1. Specifically, the lysine residue at position 13 in the amino acid sequence as set forth in SEQ ID NO: 1, which is present in β-sheet 1, is located at a position where it can readily interact with glutamic acid at position 27 present in β-sheet 2. Moreover, the lysine residue at position 22 in the amino acid sequence as set forth in SEQ ID NO: 1, which is present in the loop region between β-sheet 1 and β-sheet 2, is located at a position where it can readily interact with aspartic acid at position 20 present in the same loop region. Furthermore, the lysine residue at position 29 in the amino acid sequence as set forth in SEQ ID NO: 1 is located at a position where it can readily interact with glutamic acid at position 8 and/or threonine at position 11 present in β-sheet 1. Thus, substitution of the lysine residues at positions 13, 22, and 29 in the amino acid sequence as set forth in SEQ ID NO: 1 with an amino acid that forms an ionic bond or a hydrogen bond with glutamic acid, aspartic acid, and/or threonine at position 11 (i.e., a basic amino acid or a hydroxyl group-containing amino acid) is assumed to achieve improved alkali stability by the interactions between these amino acids. This is in line with the experimental result shown above that while PL-050 and PL-052 were found to achieve improved alkali stability, PL-051 and PL-053 to PL-056 were found to achieve no improvement in alkali stability.

That is, the foregoing results revealed that improved alkali stability can be achieved by substituting at least two or more of the lysine residues at positions 7, 13, 22, and 29 in the amino acid sequence as set forth in SEQ ID NO: 1 with a basic amino acid or a hydroxyl group-containing amino acid.

TABLE 5

| | Modified Sites and Substituting Amino Acids in Amino Acid Sequence as Set Forth in SEQ ID NO: 1 | | | | | | | Residual Activity (%) after Alkali Treatment |
|---|---|---|---|---|---|---|---|---|
| | Position 2 | Position 7 | Position 13 | Position 22 | Position 29 | Position 48 | Position 67 | |
| Wild-Type (PL-014) | T | K | K | K | K | K | K | 61.5 |
| Modified Products | | | | | | | | |
| PL-024 | | R | R | R | R | R | R | 79.6 |
| PL-026 | K | R | R | | | | | 63.8 |
| PL-027 | | R | R | R | | | | 73.8 |
| PL-028 | K | | | | R | R | R | 54.6 |
| PL-035 | | R | R | | | | | 63.3 |
| PL-036 | K | R | R | R | | | | 73.9 |
| PL-038 | R | R | R | R | R | R | R | 79.9 |
| PL-043 | R | | | | | | | 61.3 |
| PL-044 | K | | | R | | | | 60.1 |
| PL-045 | R | | | R | | | | 60.6 |
| PL-046 | K | R | | R | | | | 63.9 |
| PL-047 | K | | R | R | | | | 66.9 |
| PL-048 | K | | R | R | R | | | 76.3 |
| PL-049 | K | R | R | R | R | | | 81.6 |
| PL-050 | K | R | R | T | | | | 70.3 |
| PL-051 | K | R | R | L | | | | 60.5 |
| PL-052 | K | R | R | H | | | | 64.2 |
| PL-053 | K | R | R | E | | | | 55.6 |
| PL-054 | K | R | R | Q | | | | 57.1 |
| PL-055 | K | R | R | F | | | | 58.7 |
| PL-056 | K | R | R | A | | | | 56.4 |
| PL-057 | K | R | R | | R | | | 70.6 |
| PL-058 | K | R | | R | R | | | 76.4 |
| PL-059 | K | R | | | R | | | 64.3 |
| PL-060 | K | T | R | R | | | | 69.2 |

In the table, the blank fields in the columns of amino acid sites for each of the modified products indicate that no mutations were introduced (i.e., T at position 2; K at positions 7, 13, 22, 29, 48, and 67).

Example 2

Production of Multidomain Polypeptides of Modified Product of Immunoglobulin-Binding Domain 4 and Evaluation of Binding Capacity and Alkali Stability

[Construction of Multidomain Polypeptide Expression Plasmids and Protein Expression]

The DNA sequence of a modified product PL-024 chimeric protein contains a translation initiation codon having NdeI recognition sequence (CATATG) and a sequence encoding an artificial N-terminal sequence "MAQHDEAGLAL", followed by a sequence encoding a modified domain of the immunoglobulin kappa light chain-binding domain of Protein L, and EcoO109I recognition sequence (GGGGCCT) in a sequence encoding an artificial sequence "NIKFAGAL" at the C-terminus, and further contains 21 residues of the modified C-terminal sequence of the third α-helix of the immunoglobulin Fc-binding C-domain derived from Protein A, and lastly contains a sequence encoding an artificial C-terminal sequence "KKK", as well as a translation stop codon and BamHI recognition sequence. This cDNA of the PL-024 chimeric protein was inserted into the cloning site of pUC19 plasmid from which the EcoO109I cleavage site of the plasmid had been deleted in advance, and the resulting plasmid was used to construct multidomain polypeptide cDNAs.

A cDNA fragment consisting only of a modified domain of the immunoglobulin kappa light chain-binding domain of Protein L having EcoO109I recognition sequence at both the N- and C-termini was prepared by PCR using the cDNA of the modified product PL-024 as a template, and using synthetic oligo-DNAs oligo210 (SEQ ID NO: 34) and oligo211 (SEQ ID NO: 35) as primers. Next, pUC19 plasmid into which the above-described cDNA of the PL-024 chimeric protein had been subcloned was cleaved with EcoO109I, the cleavage site was dephosphorylated by alkaline phosphatase, and then the above-described PCR fragment was inserted into this site by a ligation reaction. A clone containing one fragment inserted by this reaction was obtained as the cDNA of a dimeric chimeric protein containing two linked modified domains of the immunoglobulin kappa light chain-binding domain of Protein L, 21 residues of the modified C-terminal sequence of the third α-helix of the immunoglobulin Fc-binding C-domain derived from Protein A (SEQ ID NO: 17), and the artificial C-terminal sequence (SEQ ID NO: 18) in this order from the N-terminus. Similarly, a clone containing three inserted fragments was obtained as the cDNA of a tetrameric chimeric protein, and a clone containing five inserted fragments was obtained as the cDNA of a hexameric chimeric protein.

The 21 residues of the modified C-terminal sequence of the third α-helix of the immunoglobulin Fc-binding C-domain derived from Protein A may also be a short sequence such as two residues "PK" or six residues "PKKKKK". The C-terminal sequence to be added has been confirmed to have no effect upon the alkali stability of the multidomain polypeptide of the modified product. The C-terminal sequence to be added is not limited to the modified sequence of the third α-helix of the immunoglobulin Fc-binding C-domain derived from Protein A, and may be any sequence containing many amino acid residues that are likely to react in the immobilization on a gel support, which allows orientation control of the modified product for immobilization on the gel.

From pUC19 plasmid into which tetrameric PL-424 or hexameric PL-624 thus obtained had been subcloned, each of the cDNAs was cut with restriction enzymes NdeI and BamHI, and inserted into the NdeI-BamHI site of the *Escherichia coli* expression vector pET9a to construct an expression plasmid. The nucleic acid sequence of each of the expression plasmids was analyzed with a CEQ 8000 DNA sequencer (Beckman Coulter, Inc.) to confirm that the sequence was as designed. Next, BL21 (DE3) competent cells (Merck Ltd.) were transformed with each of the expression plasmids to obtain a strain expressing each of the multidomain polypeptides.

Each of the expression strains was seed-cultured for 12 hours in LB medium containing 25 mg/L of kanamycin and 2.0% glucose. The resulting seed culture medium was inoculated into 2×TY medium containing 25 mg/L of kanamycin and 0.8% glucose, and cultured at 37° C. for 16 hours to express a multidomain polypeptide of interest. Then, the culture medium was centrifuged to collect *Escherichia coli* cells. Next, the collected *Escherichia coli* cells were suspended in 50 mM MES buffer (pH 6.0), the suspension was sonicated to disrupt the *Escherichia coli* cells, and then the sonicated suspension was centrifuged to collect the multidomain polypeptide of interest in the supernatant. Each of the resulting supernatants as a cell extract was subjected to SDS-PAGE, which confirmed that the multidomain polypeptide of interest was produced in the position of the corresponding molecular weight. The amino acid sequence of the obtained tetrameric PL-424 is set forth in SEQ ID NO: 36, and the amino acid sequence of the obtained hexameric PL-624 is set forth in SEQ ID NO: 37.

[Purification of Multidomain Polypeptides and Purity Assay]

The cell extract of each of the multidomain polypeptides PL-424 and PL-624 was adjusted to pH 6.0, and then applied to a cation exchanger SP-Sepharose Fast Flow (GE Healthcare KK) column in the same manner as described in Referential Example 1 above. The column was washed with 20 mM phosphate buffer (pH 6.0), and then the protein was eluted with a linear gradient of 0.2 M NaCl. Elution fractions containing the multimer of interest were collected and adjusted to pH 8, and then added to an anion exchanger GigaCap Q (Tosoh Corporation) column. The column was washed with 20 mM phosphate buffer (pH 7.8), and then the multidomain polypeptide of interest was eluted with a linear gradient of 0.35 M NaCl. Each of the eluates was subjected to SDS-PAGE to determine the purity; the results confirmed that each of the multidomain polypeptides was purified as a single band in the position of the theoretical molecular weight.

[Immobilization on Gel Support and Evaluation by Immunoglobulin Binding Capacity Measurement]

Each of the multidomain polypeptides PL-424 and PL-624 thus purified was immobilized on a formyl-activated agarose gel support at a concentration of 10 mg/mL gel, in accordance with a conventional method. The reaction solution after the immobilization was collected, and the immobilization efficiency was measured. As a result, PL-424 had an immobilization efficiency of 97.3%, and PL-624 had an immobilization efficiency of 98.0%. Next, the human IgG binding capacity of each of the immobilized gel supports was measured in the same manner as described in Referential Example 1 above. For comparison, Capto L (GE Healthcare KK) having a tetramer (Protein L) with the native sequence immobilized thereon at 10 mg/mL gel was used, and the human IgG binding capacity was similarly measured. The results are shown in Table 6. Furthermore, a PBS solution containing purified Fab prepared by papain treatment of human IgG at a concentration of 20 mg/mL was added to each of the immobilized gels, and the mixture was shaken for 1 hour. Then, the capacity was measured in the same manner as used for human IgG The amount of Fab was determined using a specific absorption coefficient of 13.5 (1 $g^{-1}$ $cm^{-1}$).

The human IgG binding capacity of multidomain polypeptide PL-424 (the number of domains: 4) was 144% that of single domain polypeptide PL-024, and the human IgG binding capacity of multidomain polypeptide PL-624 (the number of domains: 6) was 151% that of single domain polypeptide PL-024, and these multidomain polypeptides were found to exhibit higher capacities than that of the single domain polypeptide. It is worthy of note that the amounts of the bound Fab fragment having a molecular weight of 47 kDa were close to the amounts of bound IgG having a molecular weight of 145 kDa. The number of moles of each of IgG and the Fab fragment was calculated based on their molecular weight. As a result, the number of moles of IgG bound to 10 mg of PL-424 (the number of domains: 4) was 632 nmol, and the number of moles of IgG bound to 10 mg of PL-624 (the number of domains: 6) was 661 nmol. On the other hand, the number of moles of the Fab fragment bound to 10 mg of PL-424 (the number of domains: 4) was 1540 nmol, and the number of moles of the Fab fragment bound to 10 mg of PL-624 (the number of domains: 6) was 1615 nmol. That is, the multidomain polypeptides of the invention were revealed to have a binding capacity for the Fab fragment markedly higher than that for IgG This is believed to be because Fab has a small molecular size, and thus, steric hindrance is unlikely to occur upon binding.

On the other hand, as compared to Capto L (GE Healthcare KK) having the multidomain polypeptide with the native sequence (the number of domains: 4) (Protein L) immobilized thereon at 10 mg/mL gel, each of the multimers of the present invention had an amount of the bound Fab fragment about 2.4 times and an amount of bound IgG about 2.2 times those of Capto L.

TABLE 6

| Designation | | Fab Binding Capacity mg/mL gel | IgG Binding Capacity mg/mL gel |
|---|---|---|---|
| PL-424 | Tetramer | 72.4 | 91.6 |
| PL-624 | Hexamer | 75.9 | 95.8 |
| CaptoL (Comparative Example) | Tetramer (Native Form) | 30.9 | 43.6 |

[Evaluation of Stability of Multidomain Polypeptides Immobilized on Gel Support under Alkaline pH Conditions]

The gel support having each of the multidomain polypeptides immobilized thereon was replaced with an aqueous solution of 0.1 M NaOH, and then incubated at 25° C. for 17 hours. Then, the gel support was washed with PBS three times, and the human IgG binding capacity was measured under the same conditions as described above. Using the amount of IgG bound to each support before the alkali treatment as 100%, the ratio of the amount of bound IgG remaining after 17 hours of the treatment was determined as the residual activity (%) after the alkali treatment. The results are shown in Table 7.

Multidomain polypeptides PL-424 (the number of domains: 4) and PL-624 (the number of domains: 6) were found to exhibit alkali stability substantially equivalent to that of single domain polypeptide PL-024. As compared to Capto L of the multidomain polypeptide with the native sequence (the number of domains: 4), PL-424 was found to have alkali stability 1.4 times higher than that of Capto L, and PL-624 was found to have alkali stability 1.5 times higher than that of Capto L.

TABLE 7

| Designation | | Residual Activity (%) after Alkali Treatment |
|---|---|---|
| PL-424 | Tetramer | 79.3 |
| PL-624 | Hexamer | 83.8 |
| CaptoL (Comparative Example) | Tetramer (Native Form) | 55.3 |

Example 3

Production of Modified Product of Immunoglobulin-Binding Domain 3 and Evaluation of Binding Capacity and Alkali Stability

[Production of Modified Product]

Next, with the aim of improving the alkali stability, immunoglobulin-binding domain 3 was used as a basic sequence to prepare a modified product in which the four lysine residues at positions 7, 13, 22, and 29 were substituted with arginine in the immunoglobulin-binding domain 3 (SEQ ID NO: 2).

[Preparation of PL-061 Expression Plasmid]

A cDNA fragment encoding a sequence of immunoglobulin-binding domain 3 up to position 28 in which the lysine residues at positions 7, 13, and 22 were substituted with arginine, and the amino acid at position 23 was isoleucine was prepared by PCR using the PL-024 expression plasmid as a template, and using synthetic oligo-DNAs oligo-178 (SEQ ID NO: 13) and oligo-334 (SEQ ID NO: 38) as primers. Moreover, a cDNA fragment encoding a sequence of immunoglobulin-binding domain 3 from position 24 in which the lysine residue at position 29 was substituted with arginine was prepared by PCR using the PL-024 expression plasmid as a template, and using oligo-335 (SEQ ID NO: 39) and oligo-191 (SEQ ID NO: 16) as primers. A cDNA encoding PL-061 was obtained by PCR using these two DNA fragments as templates, and using synthetic oligo-DNAs oligo-178 (SEQ ID NO: 13) and oligo-191 (SEQ ID NO: 16) as primers. The resulting cDNA was cleaved with NdeI and BamHI, and then inserted into the NdeI-BamHI site of pET-9a plasmid to obtain a chimeric protein PL-061 expression plasmid in which 11 residues of the artificial N-terminal sequence (SEQ ID NO: 12), 70 residues of immunoglobulin kappa light chain-binding domain 3 of Protein L in which the lysine residues at positions 7, 13, 22, and 29 were substituted with arginine in SEQ ID NO: 2, two residues of a linker sequence consisting of alanine-leucine, 21 residues of the modified C-terminal sequence of the third α-helix of the immunoglobulin Fc-binding C-domain derived from Protein A (SEQ ID NO: 17), and three residues of the artificial C-terminal sequence (SEQ ID NO: 18) were linked in this order from the N-terminus.

[Purification of Modified Product and Purity Assay]

The cell extract of the modified product PL-061 was adjusted to pH 6.0, and then applied to a cation exchanger SP-Sepharose Fast Flow (GE Healthcare KK) column in the same manner as described in Referential Example 1. The column was washed with 20 mM phosphate buffer (pH 6.0), and then the protein was eluted with a linear gradient of 0.5 M NaCl. Elution fractions containing the modified product of interest were collected and adjusted to pH 9, and then added to an anion exchanger GigaCap Q (Tosoh Corporation) column. The column was washed with 20 mM phosphate buffer (pH 7.8), and then the modified product of interest was eluted with a linear gradient of 0.3 M NaCl. The eluate was subjected to SDS-PAGE to determine the purity; the results confirmed that the modified product was purified as a single band in the position of the theoretical molecular weight.

[Immobilization on Gel Support and Evaluation by Immunoglobulin Binding Capacity Measurement]

The modified product PL-061 thus purified was immobilized on a formyl-activated agarose gel support at a concentration of 10 mg/mL gel, in accordance with a conventional method. The reaction solution after the immobilization was collected, and the immobilization efficiency was measured. As a result, the modified product showed an immobilization efficiency of 95% or more. Next, the human IgG binding capacity of the immobilized gel support was measured in the same manner as described in Referential Example 1.

The results are shown in Table 8. The results showed that the case where the four lysine residues at positions 7, 13, 22, and 29 were substituted with arginine in SEQ ID NO: 2 also achieved improved human IgG binding capacity, as in the cases using immunoglobulin-binding domain 4 above.

TABLE 8

| Designation | IgG Binding Capacity mg/mL gel |
|---|---|
| PL-061 | 59.8 |
| Wild-Type (PL-023) | 52.2 |

[Evaluation of Stability of Modified Product Immobilized on Gel Support under Alkaline pH Conditions]

The gel support having the modified product PL-061 immobilized thereon was replaced with an aqueous solution of 0.1 M NaOH, and then incubated at 25° C. for 17 hours. Then, the gel support was washed with PBS three times, and the human IgG binding capacity was measured under the same conditions as described above. Using the amount of IgG bound to the support before the alkali treatment as 100%, the ratio of the amount of bound IgG remaining after 17 hours of the treatment was determined as the residual activity (%) after the alkali treatment. The results are shown in Table 9.

The results confirmed that the alkali stability is also improved by substituting the four lysine residues at positions 7, 13, 22, and 29 with arginine in SEQ ID NO: 2.

TABLE 9

| Designation | Residual Activity (%) after Alkali Treatment |
|---|---|
| PL-061 | 63.3 |
| Wild-Type (PL-023) | 42.9 |

Although the amino acid sequences of the immunoglobulin-binding domains of Protein L derived from *Peptostreptococcus magnus* 3316 strain show high sequence homology with those of Protein L derived from *Peptostreptococcus magnus* 312 strain, the inventor of the present invention confirmed that even if the same mutations as described above are introduced into the immunoglobulin-binding domains of Protein L derived from *Peptostreptococcus magnus* 312 strain, the resulting modified products cannot achieve improved alkali stability. That is, the mutations that can improve the alkali stability as demonstrated in Examples 1 to 3 above are considered to be unique to the immunoglobulin-binding domains of Protein L derived from *Peptostreptococcus magnus* 3316 strain.

The invention claimed is:

1. A polypeptide comprising at least one immunoglobulin-binding domain shown in any of (1-1) to (1-4):

(1-1) an immunoglobulin-binding domain comprising an amino acid sequence wherein at least two or more sites selected from the group consisting of positions 7, 13, 22, and 29 in the amino acid sequence as set forth in SEQ ID NO: 1 are each substituted with a basic amino acid other than lysine or a hydroxyl group-containing amino acid;

(1-2) an immunoglobulin-binding domain comprising an amino acid sequence wherein at least two or more sites selected from the group consisting of positions 7, 13, 22, and 29 in the amino acid sequence as set forth in SEQ ID NO: 2 are each substituted with a basic amino acid other than lysine or a hydroxyl group-containing amino acid;

(1-3) an immunoglobulin-binding domain comprising an amino acid sequence wherein at least two or more sites selected from the group consisting of positions 7, 13, 22, and 29 in the amino acid sequence as set forth in SEQ ID NO: 3 are each substituted with a basic amino acid other than lysine or a hydroxyl group-containing amino acid; and (1-4) an immunoglobulin-binding domain comprising an amino acid sequence wherein at least two or more sites selected from the group consisting of positions 6, 12, 21, and 28 in the amino acid sequence as set forth in SEQ ID NO: 4 are each substituted with a basic amino acid other than lysine or a hydroxyl group-containing amino acid.

2. The polypeptide according to claim 1, which is a single domain peptide comprising one immunoglobulin-binding domain selected from the immunoglobulin-binding domains shown in (1-1) to (1-4).

3. The polypeptide according to claim 1, which is a multidomain peptide wherein two or more immunoglobulin-binding domains selected from the immunoglobulin-binding domains shown in (1-1) to (1-4) are linked.

4. The polypeptide according to claim 1, which comprises the immunoglobulin-binding domain shown in (1-1), wherein all of positions 7, 13, 22, and 29 in the amino acid sequence as set forth in SEQ ID NO: 1 are each substituted with a basic amino acid or a hydroxyl group-containing amino acid.

5. The polypeptide according to claim 1, which comprises the immunoglobulin-binding domain shown in (1-1), wherein at least two or more sites selected from the group consisting of positions 7, 13, 22, and 29 in the amino acid sequence as set forth in SEQ ID NO: 1 are each substituted with arginine or threonine.

6. The polypeptide according to claim 1, which comprises the immunoglobulin-binding domain shown in (1-2), wherein all of positions 7, 13, 22, and 29 in the amino acid sequence as set forth in SEQ ID NO: 2 are each substituted with a basic amino acid or a hydroxyl group-containing amino acid.

7. The polypeptide according to claim 1, which comprises the immunoglobulin-binding domain shown in (1-2), wherein at least two or more sites selected from the group consisting of positions 7, 13, 22, and 29 in the amino acid sequence as set forth in SEQ ID NO: 2 are each substituted with arginine or threonine.

8. The polypeptide according to claim 1, which comprises the immunoglobulin-binding domain shown in (1-3), wherein all of positions 7, 13, 22, and 29 in the amino acid sequence as set forth in SEQ ID NO: 3 are each substituted with a basic amino acid or a hydroxyl group-containing amino acid.

9. The polypeptide according to claim 1, which comprises the immunoglobulin-binding domain shown in (1-3), wherein at least two or more sites selected from the group consisting of positions 7, 13, 22, and 29 in the amino acid sequence as set forth in SEQ ID NO: 3 are each substituted with arginine or threonine.

10. The polypeptide according to claim 1, which comprises the immunoglobulin-binding domain shown in (1-4), wherein all of positions 6, 12, 21, and 28 in the amino acid sequence as set forth in SEQ ID NO: 4 are each substituted with a basic amino acid or a hydroxyl group-containing amino acid.

11. The polypeptide according to claim 1, which comprises the immunoglobulin-binding domain shown in (1-4), wherein at least two or more sites selected from the group consisting of positions 6, 12, 21, and 28 in the amino acid sequence as set forth in SEQ ID NO: 4 are each substituted with arginine or threonine.

12. A deoxyribonucleic acid (DNA) encoding the polypeptide according to claim 1.

13. A recombinant vector comprising the DNA according to claim 12.

14. A transformant obtained by transforming a host with the recombinant vector according to claim 13.

15. A method for producing the polypeptide according to claim 1, comprising the step of culturing a transformant obtained by transforming a host with a recombinant vector comprising a deoxyribonucleic acid (DNA) encoding the polypeptide according to claim 1.

16. An immunoglobulin-binding support comprising the polypeptide according to claim 1 immobilized on an insoluble support.

17. A method for purifying an immunoglobulin or a fragment thereof, the method comprising contacting a solution containing an immunoglobulin or a kappa chain-containing fragment thereof, with the immunoglobulin-binding support according to claim 16.

18. A polypeptide comprising at least one immunoglobulin-binding domain shown in any of (2-1) to (2-4), and (3-1) to (3-4):

(2-1) an immunoglobulin-binding domain comprising an amino acid sequence wherein all of positions 7, 13, 22, and 29 in the amino acid sequence as set forth in SEQ ID NO: 1 are each substituted with a basic amino acid other than lysine or a hydroxyl group-containing amino acid, wherein one or more amino acids other than the amino acid-substituted sites are substituted, added, inserted, or deleted, the immunoglobulin-binding domain having a binding capacity for an immunoglobulin, and having improved alkali stability as compared to the polypeptide consisting of the amino acid sequence as set forth in SEQ ID NO: 1;

(2-2) an immunoglobulin-binding domain comprising an amino acid sequence wherein all of positions 7, 13, 22, and 29 in the amino acid sequence as set forth in SEQ ID NO: 2 are each substituted with a basic amino acid other than lysine or a hydroxyl group-containing amino acid, wherein one or more amino acids other than the amino acid-substituted sites are substituted, added, inserted, or deleted, the immunoglobulin-binding domain having a binding capacity for an immunoglobulin, and having improved alkali stability as compared to the polypeptide consisting of the amino acid sequence as set forth in SEQ ID NO: 1;

(2-3) an immunoglobulin-binding domain comprising an amino acid sequence wherein all of positions 7, 13, 22, and 29 in the amino acid sequence as set forth in SEQ ID NO: 3 are each substituted with a basic amino acid other than lysine or a hydroxyl group-containing amino acid, wherein one or more amino acids other than the amino acid-substituted sites are substituted, added, inserted, or deleted, the immunoglobulin-binding domain having a binding capacity for an immunoglobulin, and having improved alkali stability as compared to the polypeptide consisting of the amino acid sequence as set forth in SEQ ID NO: 3;

(2-4) an immunoglobulin-binding domain comprising an amino acid sequence wherein all of positions 6, 12, 21, and 28 in the amino acid sequence as set forth in SEQ ID NO: 4 are each substituted with a basic amino acid other than lysine or a hydroxyl group-containing amino acid, wherein one or more amino acids other than the amino acid-substituted sites are substituted, added, inserted, or deleted, the immunoglobulin-binding domain having a binding capacity for an immunoglobulin, and having improved alkali stability as compared to the polypeptide consisting of the amino acid sequence as set forth in SEQ ID NO: 4;

(3-1) an immunoglobulin-binding domain comprising an amino acid sequence wherein all of positions 7, 13, 22, and 29 in the amino acid sequence as set forth in SEQ ID NO: 1 are each substituted with a basic amino acid other than lysine or a hydroxyl group-containing amino acid, wherein an amino acid sequence excluding the amino acid-substituted sites has at least 80% sequence identity with the amino acid sequence as set forth in SEQ ID NO: 1, the immunoglobulin-binding domain having a binding capacity for an immunoglobulin, and having improved alkali stability as compared to the polypeptide consisting of the amino acid sequence as set forth in SEQ ID NO: 1;

(3-2) an immunoglobulin-binding domain comprising an amino acid sequence wherein all of positions 7, 13, 22, and 29 in the amino acid sequence as set forth in SEQ ID NO: 2 are each substituted with a basic amino acid other than lysine or a hydroxyl group-containing amino acid, wherein an amino acid sequence excluding the amino acid-substituted sites has at least 80% sequence identity with the amino acid sequence as set forth in SEQ ID NO: 2, the immunoglobulin-binding domain having a binding capacity for an immunoglobulin, and having improved alkali stability as compared to the polypeptide consisting of the amino acid sequence as set forth in SEQ ID NO: 2;

(3-3) an immunoglobulin-binding domain comprising an amino acid sequence wherein all of positions 7, 13, 22, and 29 in the amino acid sequence as set forth in SEQ ID NO: 3 are each substituted with a basic amino acid other than lysine or a hydroxyl group-containing amino acid, wherein an amino acid sequence excluding the amino acid-substituted sites has at least 80% sequence identity with the amino acid sequence as set forth in SEQ ID NO: 3, the immunoglobulin-binding domain having a binding capacity for an immunoglobulin, and having improved alkali stability as compared to the polypeptide consisting of the amino acid sequence as set forth in SEQ ID NO: 3; and (3-4) an immunoglobulin-binding domain comprising an amino acid sequence wherein all of positions 6, 12, 21, and 28 in the amino acid sequence as set forth in SEQ ID NO: 4 are each substituted with a basic amino acid other than lysine or a hydroxyl group-containing amino acid, wherein an amino acid sequence excluding the amino acid-substituted sites has at least 80% sequence identity with the amino acid sequence as set forth in SEQ ID NO: 4, the immunoglobulin-binding domain having a binding capacity for an immunoglobulin, and having improved alkali stability as compared to the polypeptide consisting of the amino acid sequence as set forth in SEQ ID NO: 4.

19. The polypeptide according to claim 18, which is a single domain peptide comprising one immunoglobulin-binding domain selected from the immunoglobulin-binding domains shown in (2-1) to (2-4), and (3-1) to (3-4).

20. The polypeptide according to claim 18, which is a multidomain peptide wherein two or more immunoglobulin-binding domains selected from the immunoglobulin-binding domains shown in (2-1) to (2-4), and (3-1) to (3-4) are linked.

21. The polypeptide according to claim 18, wherein at least two or more sites selected from the group consisting of positions 7, 13, 22, and 29 in the amino acid sequence as set forth in SEQ ID NO: 1 are each substituted with arginine or threonine.

22. The polypeptide according to claim 18, wherein at least two or more sites selected from the group consisting of positions 7, 13, 22, and 29 in the amino acid sequence as set forth in SEQ ID NO: 2 are each substituted with arginine or threonine.

23. The polypeptide according to claim 18, wherein at least two or more sites selected from the group consisting of positions 7, 13, 22, and 29 in the amino acid sequence as set forth in SEQ ID NO: 3 are each substituted with arginine or threonine.

24. The polypeptide according to claim 18, wherein at least two or more sites selected from the group consisting of positions 6, 12, 21, and 28 in the amino acid sequence as set forth in SEQ ID NO: 4 are each substituted with arginine or threonine.

25. A deoxyribonucleic acid (DNA) encoding the polypeptide according to claim 18.

26. A recombinant vector comprising the DNA according to claim 25.

27. A transformant obtained by transforming a host with the recombinant vector according to claim 26.

28. A method for producing the polypeptide according to claim 18, comprising the step of culturing a transformant obtained by transforming a host with a recombinant vector comprising a deoxyribonucleic acid (DNA) encoding the polypeptide according to claim 18.

29. An immunoglobulin-binding support comprising the polypeptide according to claim 18 immobilized on an insoluble support.

30. A method for purifying an immunoglobulin or a fragment thereof, the method comprising contacting a solution containing an immunoglobulin or a kappa chain-containing fragment thereof, with the immunoglobulin-binding support according to claim 29.

* * * * *